(12) United States Patent
Dutkiewicz et al.

(10) Patent No.: US 10,745,836 B2
(45) Date of Patent: Aug. 18, 2020

(54) MULTISTRATA NONWOVEN MATERIAL

(71) Applicant: GEORGIA-PACIFIC NONWOVENS LLC, Atlanta, GA (US)

(72) Inventors: Jacek Dutkiewicz, Cordova, TN (US); David Reid Murphy, Charlotte, NC (US); Alan Edward Wright, Roswell, GA (US); James Parsons, Germantown, TN (US); John Baker, Floyd, VA (US); Shiu-Kang Laurence Li, Delta (CA)

(73) Assignee: GEORGIA-PACIFIC NONWOVENS LLC, Atlanta, GA (US)

( * ) Notice: Subject to any disclaimer, the term of this patent is extended or adjusted under 35 U.S.C. 154(b) by 448 days.

(21) Appl. No.: 14/776,408

(22) PCT Filed: Mar. 17, 2014

(86) PCT No.: PCT/US2014/030632
§ 371 (c)(1),
(2) Date: Sep. 14, 2015

(87) PCT Pub. No.: WO2014/145804
PCT Pub. Date: Sep. 18, 2014

(65) Prior Publication Data
US 2016/0040337 A1  Feb. 11, 2016

Related U.S. Application Data

(60) Provisional application No. 61/802,005, filed on Mar. 15, 2013.

(51) Int. Cl.
*D04H 1/559* (2012.01)
*D04H 1/407* (2012.01)
(Continued)

(52) U.S. Cl.
CPC .......... *D04H 1/559* (2013.01); *A61F 13/534* (2013.01); *B32B 5/022* (2013.01); *B32B 5/08* (2013.01);
(Continued)

(58) Field of Classification Search
CPC ......... B32B 5/08; B32B 38/164; B32B 37/24; B32B 5/022; B32B 5/26;
(Continued)

(56) References Cited

U.S. PATENT DOCUMENTS 4,634,621 A    1/1987  Manning et al.
5,139,841 A *  8/1992  Makoui ............ A61F 13/15699
                                              428/109
(Continued)

FOREIGN PATENT DOCUMENTS

WO    WO 2005/102682 A2    11/2005

OTHER PUBLICATIONS

Lee et al., "Antimicrobial and Blood Repellent Finishes for Cotton and Nonwoven Fabrics Based on Chitosan and Fluoropolymers," Textile Research Journal, 69 (2): 104-112, Feb. 1999.*
(Continued)

*Primary Examiner* — Camie S Thompson

(57) ABSTRACT

The presently disclosed subject matter relates to a multilayer nonwoven material. More particularly, the presently disclosed subject matter relates to multilayered structures including, but not limited to, two, three, or four layers to form the nonwoven material. The multilayered structure can include a first layer comprising continuous filaments and a second layer comprising bonded fibers. The continuous filaments can be synthetic filaments. The fibers can be cellulosic fibers, noncellulosic fibers, or combinations thereof. Certain layers can also contain a binder material.

37 Claims, 21 Drawing Sheets

Example of wipe structure

(51) Int. Cl.
*B32B 5/26* (2006.01)
*B32B 5/02* (2006.01)
*B32B 38/00* (2006.01)
*B32B 5/08* (2006.01)
*B32B 37/24* (2006.01)
*D04H 1/425* (2012.01)
*D04H 1/593* (2012.01)
*A61F 13/534* (2006.01)
*D04H 1/4374* (2012.01)
*A61F 13/511* (2006.01)

(52) U.S. Cl.
CPC ............... *B32B 5/26* (2013.01); *B32B 37/24* (2013.01); *B32B 38/164* (2013.01); *D04H 1/407* (2013.01); *D04H 1/425* (2013.01); *D04H 1/4374* (2013.01); *D04H 1/593* (2013.01); *A61F 2013/51178* (2013.01); *B32B 2250/20* (2013.01); *B32B 2262/0253* (2013.01); *B32B 2262/0261* (2013.01); *B32B 2262/0276* (2013.01); *B32B 2262/062* (2013.01); *B32B 2262/067* (2013.01); *B32B 2262/12* (2013.01); *B32B 2262/14* (2013.01); *B32B 2307/3065* (2013.01); *B32B 2307/7163* (2013.01); *B32B 2307/726* (2013.01); *B32B 2307/758* (2013.01); *B32B 2555/00* (2013.01)

(58) Field of Classification Search
CPC .... B32B 2307/7163; B32B 2307/3065; B32B 2262/14; B32B 2262/12; B32B 2262/067; B32B 2262/062; B32B 2262/0276; B32B 2262/0261; B32B 2250/20; B32B 2307/758; B32B 2555/00; Y10T 442/66; Y10T 442/668; Y10T 442/681; Y10T 442/692; Y10T 442/698; Y10T 428/24099; Y10T 428/253; Y10T 428/197; Y10T 428/2929; Y10T 428/24091; Y10T 428/27; Y10T 442/641; Y10T 442/664; Y10T 442/159; A61F 13/534; A61F 13/51178; D21H 5/10; D04H 1/407; D04H 1/559; D04H 1/4374; D04H 1/593; D04H 1/425; D04H 13/534; D04H 3/16; D04H 13/006; D04H 13/007; D04H 3/12
USPC ....... 442/381–393, 401, 411, 416, 172, 361; 604/358–402; 428/172, 110, 326, 373, 428/109, 381; 19/302; 156/306.6, 324, 156/163, 164, 313, 307.3
See application file for complete search history.

(56) References Cited

U.S. PATENT DOCUMENTS

| | | | | |
|---|---|---|---|---|
| 2003/0097105 | A1* | 5/2003 | Chen | A61F 13/47218 604/378 |
| 2003/0129908 | A1* | 7/2003 | Wadsworth | B32B 5/26 442/382 |
| 2005/0244619 | A1* | 11/2005 | Kauschke | A61F 13/512 428/195.1 |
| 2011/0087185 | A1* | 4/2011 | Wohlke | A61F 13/47 604/367 |
| 2014/0142533 | A1* | 5/2014 | Peltier | A61F 13/5633 604/391 |
| 2014/0155854 | A1* | 6/2014 | MacDonald | D04H 1/435 604/372 |
| 2015/0313766 | A1* | 11/2015 | Miao | A61F 13/475 604/385.101 |

OTHER PUBLICATIONS

International Search report dated Jun. 6, 2014 in PCT/US2014/030632.

* cited by examiner

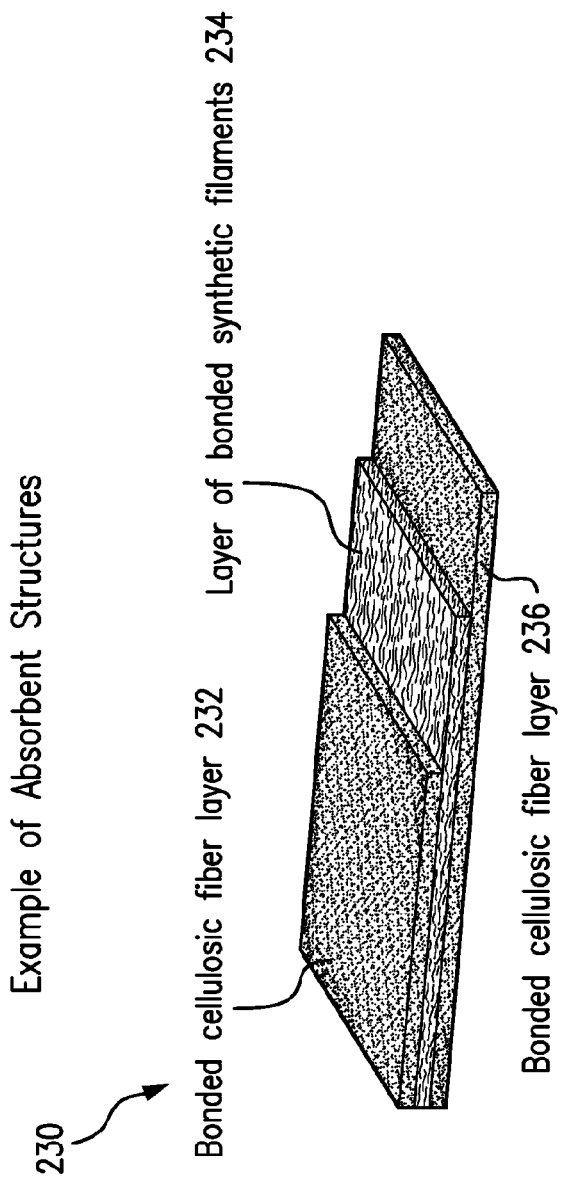

MULTISTRATA NONWOVEN MATERIAL

CROSS-REFERENCE TO RELATED APPLICATIONS

This application is a U.S. National Stage Patent Application under 35 U.S.C. § 371 of International Application No. PCT/US2014/030632, filed on Mar. 17, 2014, which claims priority to U.S. Provisional Patent Application No. 61/802,005 filed Mar. 15, 2013, which is incorporated by reference herein in its entirety for all purposes.

FIELD OF THE INVENTION

The presently disclosed subject matter relates to a multi-layered nonwoven material which can be used across a wide range of applications, including but not limited to absorbent products, wipes, filtration products, and personal care products such as feminine care products and adult incontinence products. The presently disclosed nonwoven material provides improved stretch or elongation, drape, acquisition, distribution, and retention qualities, amongst other things as needed.

BACKGROUND OF THE INVENTION

Nonwoven materials are well-known in the art for various uses. Specifically, nonwoven materials are used in a variety of applications including feminine care products, dispersible wipes, and the like. The use of cellulosic or cellulose fibers in a range of consumer products is well known. For example, cellulosic fibers can be used in paper products including bags, tags, toweling, tissue, map papers, paper patterns, napkins, poster papers, filter papers, and in many other grades or uses of paper. Cellulosic fibers are also utilized in structures or components of disposable absorbent products such as diaper liners, diaper wrap sheets, diaper absorbent structures, feminine napkin wrap sheets, disposable hospital bed pads, and the like.

Continuous improvements have been made over time, including for example, increasing absorption while making thinner materials, or improving dispersibility while retaining absorptive capability. Many of these improvements are made with an eye towards a more cost-effective product for both the manufacturer and the consumer.

Despite the various improvements made in the nonwoven structures to date, there remains a need in the art for a nonwoven material that balances all of the desired features noted above. The disclosed subject matter addresses these needs, amongst others.

SUMMARY OF THE INVENTION

The presently disclosed subject matter advantageously provides for an economical nonwoven material that has improved stretch or elongation, drape, acquisition, distribution, and retention qualities, amongst other things, as needed.

In accordance with one aspect of the disclosed subject matter, a multilayer nonwoven material is provided. The multilayer material includes a first layer comprising continuous filaments and a second layer adjacent to the first layer comprising fibers. The nonwoven material has an elongation at peak load that is less than half a total elongation. The continuous filaments can be bonded continuous filaments. The continuous filaments can be bonded by, for example, hydroentangling or thermal bonding.

In accordance with exemplary embodiments of the disclosed subject matter, the fibers can be formed using an airlaid process or a wet laid process. The nonwoven material can be embossed with a pattern. The nonwoven material can also include a surface treatment for improving wettability. A functional additive, such as a superabsorbent particle, an odor control agent, a microbial agent, or a fire retardant agent, can also be included in the nonwoven material.

The continuous filaments in the first layer can be, for example, synthetic filaments. In accordance with exemplary embodiments of the disclosed subject matter, the synthetic filaments can be, for example, polypropylene, polyethylene, or polyester. In accordance with other embodiments of the disclosed subject matter, the continuous filaments can be bicomponent filaments, natural polymer filaments, or regenerated cellulose filaments. The continuous filaments can be, for example, spundbond filaments or meltblown filaments.

The fibers in the second layer can be, for example, cellulosic fibers. In accordance with exemplary embodiments of the disclosed subject matter, the cellulosic fibers can be, for example, natural fibers or wood pulp fibers. In other embodiments, the fibers can be regenerated cellulose fibers or synthetic fibers. The fibers can be short fibers. In accordance with certain embodiments of the disclosed subject matter, the fibers can be bonded with a binder.

In accordance with embodiments of the disclosed subject matter, the multilayer nonwoven material can include at least one or more additional layers comprising bonded continuous filaments. Alternatively or in addition, the nonwoven material can include one or more layers comprising bonded fibers. The first layer can be bonded to the second layer using a binder.

In another aspect, the disclosed subject matter provides a wipe. The wipe includes a multilayer nonwoven material having a first layer comprising continuous filaments and a second layer adjacent to the first layer comprising bonded fibers. The multilayer nonwoven material has an elongation at peak load that is less than half a total elongation. The wipe can be, for example, a dry wipe, a wet wipe, a personal care wipe, or an industrial wipe.

In accordance with another aspect of the disclosed subject matter, a personal care product is provided. The personal care product includes a multilayer nonwoven material having a first layer comprising continuous filaments and a second layer adjacent to the first layer comprising bonded fibers. The multilayer nonwoven material has an elongation at peak load that is less than half a total elongation. The personal care product can be, for example, a diaper, a feminine care product, or an adult incontinence product.

In accordance with another aspect of the disclosed subject matter, a method for forming a multilayer nonwoven material is provided. The method includes producing a first layer comprising continuous filaments, producing a second layer comprising bonded fibers, and binding the first layer to the second layer.

The first layer can be produced by, for example, spunbonding or meltblowing. The production of the first layer can include binding the continuous filaments by hydroentangling or thermal bonding.

The second layer can be produced by, for exmapling, using an airlaid process or a wet laid process. A functional additive can be added to the nonwoven material. In accordance with embodiments of the disclosed subject matter, the method can also include embossing the nonwoven material with a pattern. The nonwoven material can also be treated with a surface treatment to improve wettability.

It is to be understood that both the foregoing general description and the following detailed description are exemplary and are intended to provide further explanation of the disclosed subject matter.

The accompanying drawings, which are incorporated in and constitute part of this specification, are included to illustrate and provide a further understanding of the disclosed subject matter.

BRIEF DESCRIPTION OF THE DRAWINGS

FIGS. 2A-2C depict nonlimiting examples of structures contemplated by the disclosed subject matter. FIG. 2A provides examples of structures for fluid acquisition. FIG. 2B provides examples of structures for fluid retention. FIG. 2C provides an example of an absorbent structure.

DETAILED DESCRIPTION

Figure 1:
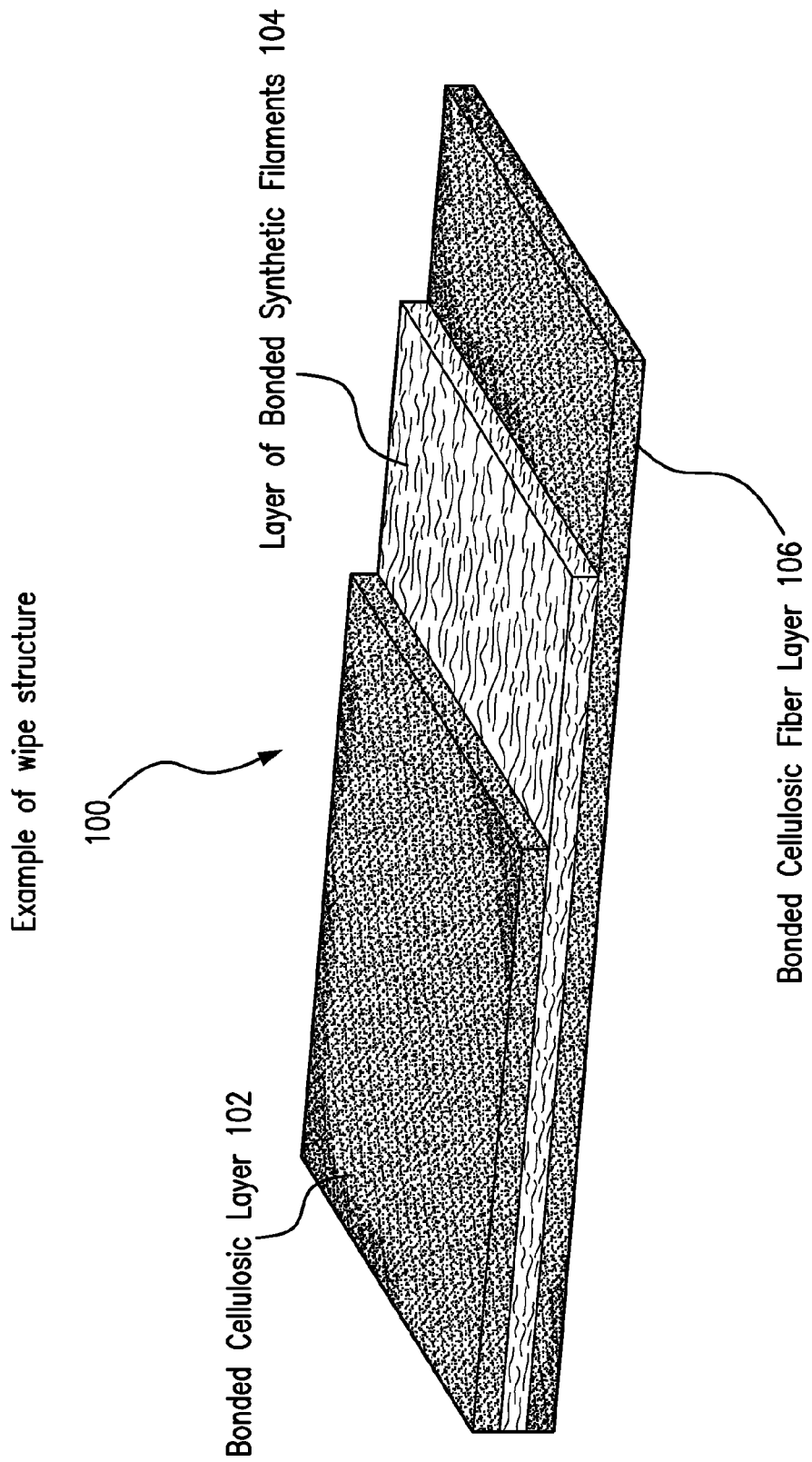
FIG. 1 depicts a nonlimiting example of a multilayer wipe structure having three layers. The first layer contains bonded cellulosic fiber. The second layer contains bonded synthetic filament. The third layer contains bonded cellulosic fiber.

The presently disclosed subject matter provides an improved nonwoven material that can be used in a variety of products. The presently disclosed subject matter also provides for a process for making such materials. These and other aspects of the disclosed subject matter are discussed more in the detailed description and non-limiting examples.

Definitions

The terms used in this specification generally have their ordinary meanings in the art, within the context of the disclosed subject matter and in the specific context where each term is used. Certain terms are defined below to provide additional guidance in describing the compositions and methods of the disclosed subject matter and how to make and use them.

As used herein, a "nonwoven" refers to a class of material, including but not limited to textiles or plastics. Nonwovens are sheet or web structures made of fiber, filaments, molten plastic, or plastic films bonded together mechanically, thermally, or chemically. A nonwoven is a material, article, or fabric made directly from a web of fiber, without the yarn preparation necessary for weaving or knitting. In a nonwoven, the assembly of fibers can be held together by one or more of the following: (1) by mechanical interlocking in a random web or mat; (2) by fusing of the fibers, as in the case of thermoplastic fibers; or (3) by bonding with a cementing medium such as an adhesive.

As used herein, a "wipe" is a type of nonwoven article suitable for cleansing or disinfecting or for applying or removing an active compound. In particular, this term refers to an article for cleansing the body, including the removal of bodily waste, or removing debris from any other surface. Wipes can be dry wipes or wet wipes (for example, with the addition of a wetting or cleansing lotion).

As used herein, the term "flushable" refers to the ability of a material, when flushed, to clear the toilet and trap and the drain lines leading to the municipal wastewater conveyance system.

As used herein, the term "dispersible" refers to the ability of a material to readily break apart in water due to physical forces. In particular, the term "dispersible" refers to the ability of a material to readily break apart due to the physical forces encountered during flushing in a common toilet, conveyance in a common wastewater system, and processing in a common treatment system.

As used herein, the term "weight percent" is meant to refer to either (i) the quantity by weight of a constituent/component in the material as a percentage of the weight of a layer of the material; or (ii) to the quantity by weight of a constituent/component in the material as a percentage of the weight of the final nonwoven material or product.

The term "basis weight" as used herein refers to the quantity by weight of a compound over a given area. Examples of the units of measure include grams per square meter as identified by the acronym "gsm".

As used herein, the terms "gli," "g/in," and "G/in" refer to "grams per linear inch" or "gram force per inch." This refers to the width, not the length, of a test sample for tensile strength testing.

As used in the specification and the appended claims, the singular forms "a," "an" and "the" include plural referents unless the context clearly dictates otherwise. Thus, for example, reference to "a compound" includes mixtures of compounds.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, such as up to 10%, in other embodiments up to 5%, and in other embodiments still up to 1% of a given value. Alternatively, particularly with respect to systems or processes, the term can mean within an order of magnitude, in other embodiments within 5-fold, and in other embodiments within 2-fold, of a value.

The disclosed subject matter relates to multilayer materials. In certain embodiments, the nonwoven structure contains at least one layer, at least two layers, or at least three layers. In accordance with one embodiment of the disclosed subject matter, a three layer structure is provided. For example, FIG. 1 illustrates an exemplary embodiment of a three layer nonwoven material in accordance with the disclosed subject matter. For purposes of explanation and not limitation, the structure 100 includes a first layer 102 containing a fiber, a second layer 104 including continuous filaments, and a third layer 106 including a fiber.

Fibers

Nonwoven materials in accordance with the disclosed subject matter can include one or more types of fibers. For example, first layer 102 and third layer 106 of structure 100 can include fibers. The fibers can be natural, synthetic, or a mixture thereof. In one embodiment, the fibers can be one or more cellulose-based fibers, one or more synthetic fibers, or a mixture thereof. Cellulose fibers can include, for example, chemically modified cellulose fibers and regenerated cellulose fibers. In accordance with embodiments of the disclosed subject matter, the fibers can be short fibers or long fibers.

Cellulosic Fibers

Any cellulose fibers known in the art, including cellulose fibers of any natural origin, such as those derived from wood pulp, can be used in one or more layers. Suitable cellulose fibers include, but are not limited to, digested fibers, such as kraft, prehydrolyzed kraft, soda, sulfite, chemi-thermal mechanical, and thermo-mechanical treated fibers, derived from softwood, hardwood or cotton linters. Other cellulose fibers include, but are not limited to, kraft digested fibers, including prehydrolyzed kraft digested fibers. Non-limiting examples of cellulosic fibers suitable for use in this disclosed subject matter are the cellulose fibers derived from softwoods, such as pines, firs, and spruces. Other suitable cellulose fibers include, but are not limited to, those derived from Esparto grass, bagasse, kemp, flax, hemp, kenaf, and other lignaceous and cellulosic fiber sources. Suitable cellulose fibers include, but are not limited to, bleached Kraft southern pine fibers sold under the trademark FOLEY FLUFFS® (Buckeye Technologies Inc., Memphis, Tenn.).

The nonwoven materials of the disclosed subject matter can also include, but are not limited to, a commercially available bright fluff pulp including, but not limited to, southern softwood fluff pulp (such as treated FOLEY FLUFFS®) northern softwood sulfite pulp (such as T 730 from Weyerhaeuser), or hardwood pulp (such as eucalyptus). The pulp can be treated FOLEY FLUFFS® from Buckeye Technologies Inc. (Memphis, Tenn.); however any absorbent fluff pulp or mixtures thereof can be used. In other embodiments, wood cellulose, cotton linter pulp, chemically modified cellulose such as cross-linked cellulose fibers and highly purified cellulose fibers can be used. In other embodiments, the pulps are FOLEY FLUFFS® FFTAS (also known as FFTAS or Buckeye Technologies FFT-AS pulp), and Weyco CF401. The fluff fibers can be blended with synthetic fibers, for example polyester, nylon, polyethylene or polypropylene.

In certain embodiments, the cellulose fibers in a particular layer comprise from about 50 to about 100 percent by weight of a layer. In one embodiment, the cellulose fibers in a particular layer comprise from about 70 to about 100 percent by weight of a layer, from about 80 to about 100 percent by weight of a layer, from about 90 to about 100 percent by weight of a layer, from about 50 to about 95 percent by weight of a layer, from about 70 to about 95 percent by weight of a layer, from about 80 to about 90 percent by weight of a layer, or from about 80 to about 95 percent by weight of a layer. In an alternate embodiment, the cellulose fibers in a particular layer comprise from about 0 to about 50 percent by weight of a layer, from about 10 to about 50 percent by weight of a layer, from about 20 to about 50 percent of a layer, from about 30 to about 50 percent of a layer, or from about 10 to about 40 percent by weight of a layer.

In accordance with embodiments of the disclosed subject matter, the fibers can be short fibers. As used herein, the term "short fiber" refers to a fiber having a length of less than about 20 mm. For example, layers of multilayer structures in accordance with the disclosed subject matter can contain short fibers having a length of less than about 15 mm, less than about 12 mm, or less than about 10 mm. As used herein, the term "long fibers" refers to a fiber having a length of more than about 20 mm. For example, layers of multilayer structures in accordance with the disclosed subject matter can have a length of more than about 20 mm or more than about 36 mm.

Modified Cellulose

Cellulose fibers can also include, but are not limited to, chemically modified cellulose fibers. In particular embodiments, the modified cellulose fibers can be crosslinked cellulose fibers. U.S. Pat. Nos. 5,492,759; 5,601,921; 6,159,335, all of which are hereby incorporated by reference in their entireties, relate to chemically treated cellulose fibers that can be used in accordance with the disclosed subject matter. In certain embodiments, the modified cellulose fibers can include a polyhydroxy compound. Non-limiting examples of polyhydroxy compounds include glycerol, trimethylolpropane, pentaerythritol, polyvinyl alcohol, partially hydrolyzed polyvinyl acetate, and fully hydrolyzed polyvinyl acetate. In certain embodiments, the fiber can be treated with a polyvalent cation-containing compound. In one embodiment, the polyvalent cation-containing compound is present in an amount from about 0.1 weight percent to about 20 weight percent based on the dry weight of the untreated fiber. In particular embodiments, the polyvalent cation containing compound can be a polyvalent metal ion salt. In certain embodiments, the polyvalent cation containing compound is selected from the group consisting of aluminum, iron, tin, salts thereof, and mixtures thereof. In another embodiment, the polyvalent metal is aluminum.

Polyvalent metal salts including transition metal salts can be used. Non-limiting examples of suitable polyvalent metals include beryllium, magnesium, calcium, strontium, barium, titanium, zirconium, vanadium, chromium, molybdenum, tungsten, manganese, iron, cobalt, nickel, copper, zinc, aluminum and tin. Other ions include aluminum, iron and tin. Suitable metal ions can have oxidation states of +3 or +4. Salts containing the polyvalent metal ion can be employed. Non-limiting examples of suitable inorganic salts of such metals include chlorides, nitrates, sulfates, borates, bromides, iodides, fluorides, nitrides, perchlorates, phosphates, hydroxides, sulfides, carbonates, bicarbonates, oxides, alkoxides phenoxides, phosphites, and hypophosphites. Non-limiting examples of suitable organic salts of such metals include formates, acetates, butyrates, hexanoates, adipates, citrates, lactates, oxalates, propionates, salicylates, glycinates, tartrates, glycolates, sulfonates, phosphonates, glutamates, octanoates, benzoates, gluconates, maleates, succinates, and 4,5-dihydroxy-benzene-1,3-disulfonates. In addition to the polyvalent metal salts, other compounds such as complexes of the above salts include, but are not limited to, amines, ethylenediaminetetra-acetic acid (EDTA), diethylenetriaminepenta-acetic acid (DIPA), nitrilotri-acetic acid (NTA), 2,4-pentanedione, and ammonia can be used.

In one embodiment, the cellulose pulp fibers can be chemically modified cellulose pulp fibers that have been softened or plasticized to be inherently more compressible than unmodified pulp fibers. The same pressure applied to a plasticized pulp web can result in higher density than when applied to an unmodified pulp web. Additionally, the densified web of plasticized cellulose fibers is inherently softer than a similar density web of unmodified fiber of the same wood type. Softwood pulps can be made more compressible using cationic surfactants as debonders to disrupt interfiber associations. Use of one or more debonders can facilitate the disintegration of the pulp sheet into fluff in the airlaid process. Examples of debonders include, but are not limited to, those disclosed in U.S. Pat. Nos. 4,432,833, 4,425,186 and 5,776,308, all of which are hereby incorporated by reference in their entireties. One example of a debonder-treated cellulose pulp is FFLE+. Plasticizers for cellulose, which can be added to a pulp slurry prior to forming wetlaid sheets, can also be used to soften pulp, although they act by a different mechanism than debonding agents. Plasticizing agents act within the fiber, at the cellulose molecule, to make flexible or soften amorphous regions. The resulting fibers can be characterized as limp. Since the plasticized fibers lack stiffness, the comminuted pulp can be easier to densify compared to fibers not treated with plasticizers. Plasticizers include, but are not limited to, polyhydric alcohols such as glycerol, low molecular weight polyglycol such as polyethylene glycols and polyhydroxy compounds. These and other plasticizers are described and exemplified in U.S. Pat. Nos. 4,098,996, 5,547,541 and 4,731,269, all of which are hereby incorporated by reference in their entireties. Ammonia, urea, and alkylamines are also known to plasticize wood products, which mainly contain cellulose (A. J. Stamm, Forest Products Journal 5(6):413, 1955, hereby incorporated by reference in its entirety).

In particular embodiments, the cellulose fibers can be modified with a polycationic polymer. Such polymers include, but are not limited to, homo- or copolymers of at least one monomer including a functional group. The polymers can have linear or branched structures. Non-limiting examples of polycationic polymers include cationic or cationically modified polysaccharides, such as cationic starch derivatives, cellulose derivatives, pectin, galactoglucomannan, chitin, chitosan or alginate, a polyallylamine homo- or copolymer, optionally including modifier units, for example polyallylamine hydrochloride; polyethylenemine (PEI), a polyvinylamine homo- or copolymer optionally including modifier units, poly(vinylpyridine) or poly(vinylpyridinium salt) homo- or copolymer, including their N-alkyl derivatives, polyvinylpyrrolidone homo- or copolymer, a polydiallyldialkyl, such as poly(N,N-diallyl-N,N-dimethylammonium chloride) (PDDA), a homo- or copolymer of a quaternized di-$C_1$-$C_4$-alkyl-aminoethyl acrylate or methacrylate, for example a poly(2-hydroxy-3-methacryloylpropyl-tri-$C_1$-$C_2$-alkylammonium salt) homopolymer such as a poly(2-hydroxy-3-methacryloylpropyl trimethylammonium chloride), or a quatemized poly(2-dimethylaminoethyl methacrylate or a quatemized poly(vinylpyrrolidone-co-2-dimethylaminoethyl methacrylate) a poly (vinylbenzyl-tri-$C_1$-$C_4$-alkylammonium salt), for example a poly(vinylbenzyl-tri-methylammoniumchloride), polymers formed by reaction between ditertiary amines or secondary amines and dihaloalkanes, including a polymer of an aliphatic or araliphatic dihalide and an aliphatic N,N,N',N'-tetra-$C_1$-$C_4$-alkyl-alkylenediamine, a polyaminoamide (PA-MAM), for example a linear PAMAM or a PAMAM dendrimer, cationic acrylamide homo- or copolymers, and their modification products, such as poly(acrylamide-co-diallyldimethylammonium chloride) or glyoxal-acrylamide-resins; polymers formed by polymerisation of N-(dialkylaminoalkyl)acrylamide monomers, condensation products between dicyandiamides, formaldehyde and ammonium salts, typical wet strength agents used in paper manufacture, such as urea-formaldehyde resins, melamine-formaldehyde resins, polyvinylamine, polyureide-formaldehyde resins, glyoxal-acrylamide resins and cationic materials obtained by the reaction of polyalkylene polyamines with polysaccharides such as starch and various natural gums, as well as 3-hydroxyazetidinium ion-containing resins, which are obtained by reacting nitrogen-containing compounds (e.g., ammonia, primary and secondary amine or N-containing polymers) with epichlorohydrine such as polyaminoamide-epichlorohydrine resins, polyamine-epichlorohydrine resins and aminopolymer-epichlorohydrine resins.

Regenerated fibers can also be used in accordance with the presently disclosed subject matter. Regenerated fibers can include viscose, rayon, acetate, lyocell, Tencel®, Modal®, and other fibers known to those skilled in the art. Regenerated cellulose fibers can be suitable for use in certain applications (e.g., nonwoven applications), due at least in part to their soft feel, water absorption, microdiameter size, biodegradability and the ability of these fibers to be combined in the spinning process to form either self-bonded or spunlaced webs. Fibers made from pulp with high hemicellulose content can be suitable for such applications at least in part because of added interfiber bonding attributed to hemicellulose.

Regenerated fibers can include fibers formed from naturally occurring materials such as cellulose. The cellulose can be a component of plant matter, such as, for example, leaves, wood, bark, and cotton. However, these fibers can require further chemical reprocessing to be manufactured into filaments or fibers. A solution spinning processes can be used to form fibers from cellulose.

For example, rayon fibers can be generated from cellulose through a wet solution spinning process. Rayon fibers can include cellulose having the same or similar chemical structure as naturally occurring cellulose. However, cellulose included in these fibers can have a shorter molecular chain length relative to naturally occurring cellulose. For example, rayon fibers can include cellulose in which substituents have replaced not more than about 15 percent of hydrogens of hydroxyl groups in the cellulose. Examples of rayon fibers include viscose rayon fibers and cuprammonium rayon fibers.

Acetate fibers can be generated from cellulose using a dry solution spinning process. Acetate fibers can include a chemically modified form of cellulose in which various hydroxyl groups are replaced by acetyl groups.

Lyocell is a regenerated cellulose material that can be generated using an organic solvent spinning process. Lyocell can be generated by dissolving cellulose in a mixture of N-methylmorpholine-N-oxide (NMMO) and water and extruding the solution into a regenerating bath, such as water. Other solvents that can be used include ionic liquids, ionic liquid/water, ionic/organic solvent mixture. Lyocell is a generic term for a fiber composed of cellulose precipitated from organic solution in which no substitution of hydroxyl groups takes place and no chemical intermediates are formed. Lyocell fibers can be obtained, for example, from Lenzing AG (Lenzing, Austria), which manufactures and sells lyocell fibers under the name Tencel®.

Lyocell fibers can be particularly suitable for use in certain nonwoven applications because of their characteristic soft feel, water absorption, microdiameter size, biodegradability and the ability of these fibers to be combined in the spinning process to form either selfbonded or spunlaced webs. Fibers made from pulp with high hemicelluloses content can be particularly suited for such applications because of the added interfiber bonding attributed to hemicelluloses.

Certain regenerated cellulose fibers can be produced from high quality wood pulps extensively processed to remove non-cellulose components, especially hemicelluloses. For example, lyocell can be generated using such processes. Such highly-processed pulps can be referred to as dissolving grade or high $\alpha$ (high alpha) pulps, in which the term $\alpha$ can refer to the percentage of cellulose remaining after extraction with 17.5% caustic. Alpha cellulose can be determined by TAPPI 203. As such, a high $\alpha$ pulp can include a high percentage of cellulose, and a correspondingly low percentage of other components such as hemicelluloses. Some processes for generating high $\alpha$ pulps can increase the cost of regenerated cellulose fibers and products manufactured from these fibers. Cellulose for these high $\alpha$ pulps can be from both hardwoods and softwoods.

A low $\alpha$ pulp having a higher percentage of hemicelluloses can be a lower cost alternative to high $\alpha$ dissolving grade pulps. Such low $\alpha$ pulps can have a low copper number, a low lignin content, a low transition metal content and a broad molecular weight distribution. Examples of low $\alpha$ pulps are described in U.S. Pat. Nos. 6,979,113, 6,686,093, and 6,706,876, which are incorporated by reference here in their entireties. Both high alpha pulps and lower alpha pulps such as Peach® pulp, available from Weyerhaeuser Company, Federal Way, Wash., can be used in accordance with the disclosed subject matter. Some lower alpha pulps can provide the benefit of lower cost and better bonding for nonwoven textile applications because of their high hemicelluloses content.

Synthetic Fibers

In addition to the use of cellulose fibers, the presently disclosed subject matter also contemplates the use of synthetic fibers. The synthetic fibers can be monocomponent fibers, bicomponent fibers, or multicomponent fibers. For example, in accordance with embodiments of the disclosed subject matter, the synthetic fibers can be bicomponent fibers.

Bicomponent fibers having a core and sheath are known in the art. Many varieties of bicomponent fibers can be used in the manufacture of nonwoven materials, such as those produced for use in airlaid techniques. For purposes of explanation and not limitation, bicomponent fibers suitable for use in the disclosed subject matter are disclosed in U.S. Pat. Nos. 5,372,885 and 5,456,982, both of which are hereby incorporated by reference in their entireties. Examples of bicomponent fiber manufacturers include, but are not limited to, Trevira (Bobingen, Germany), Fiber Innovation Technologies (Johnson City, Tenn.) and ES Fiber Visions (Athens, Ga.).

Bicomponent fibers can incorporate a variety of polymers as their core and sheath components. In accordance with certain embodiments of the disclosed subject matter, bicomponent fibers that have a PE (polyethylene) or modified PE sheath can have a PET (polyethyleneterephthalate) or PP (polypropylene) core. In one embodiment, the bicomponent fiber has a core made of polyester and sheath made of polyethylene. The denier of the bicomponent fiber can range from about 1.0 dpf to about 4.0 dpf, and in other embodiments from about 1.5 dpf to about 2.5 dpf. The length of the bicomponent fiber is from about 3 mm to about 36 mm, in other embodiments from about 3 mm to about 12 mm, in other embodiments from about 6 mm to about 12. In particular embodiments, the length of the bicomponent fiber is from about 8 mm to about 12 mm, or about 10 mm to about 12 mm. Another bicomponent fiber is Trevira T255 which contains a polyester core and a polyethylene sheath modified with maleic anhydride. T255 has been produced in a variety of deniers, cut lengths and core-sheath configurations with some configurations having a denier from about 1.7 dpf to 2.0 dpf and a cut length of about 4 mm to 12 mm and a concentric core-sheath configuration and another bicomponent fiber being Trevira 1661, T255, 2.0 dpf and 12 mm in length. In an alternate embodiment, the bicomponent fiber is Trevira 1663, T255, 2.0 dpf, 6 mm. Bicomponent fibers can be fabricated by melt spinning. In this procedure, each molten polymer can extruded through a die, for example, a spinneret, with subsequent pulling of the molten polymer to move it away from the face of the spinneret. This is followed by solidification of the polymer by heat transfer to a surrounding fluid medium, for example chilled air, and taking up of the now solid filament. Non-limiting examples of additional steps after melt spinning can also include hot or cold drawing, heat treating, crimping and cutting. This overall manufacturing process can be carried out as a discontinuous two-step process that first involves spinning of the filaments and their collection into a tow that comprises numerous filaments. During the spinning step, when molten polymer is pulled away from the face of the spinneret, some drawing of the filament can occur, which can also be called the draw-down. This can followed by a second step where the spun fibers are drawn or stretched to increase molecular alignment and crystallinity and to give enhanced strength and other physical properties to the individual filaments. Subsequent steps can include, but are not limited to, heat setting, crimping and cutting of the filament into fibers.

In accordance with certain embodiments of the disclosed subject matter, the spinning and drawing of the core and sheath of the bicomponent fibers can be a continuous process. During the fiber manufacturing process, various materials can be added to the fiber after the melt spinning step at various subsequent steps. These additional materials can be referred to as "finish" and can include active agents such as, but not limited to, lubricants and anti-static agents. The finish can be delivered via an aqueous based solution or emulsion. Finishes can provide certain properties for both the manufacturing of the bicomponent fiber and for the user of the fiber, for example in an airlaid or wetlaid process.

References relating to fibers and filaments, including those of man-made thermoplastics, and incorporated herein by reference, are, for example: (a) Encyclopedia of Polymer Science and Technology, Interscience, New York, vol. 6 (1967), pp. 505-555 and vol. 9 (1968), pp. 403-440; (b) Kirk-Othmer Encyclopedia of Chemical Technology, vol. 16 for "Olefin Fibers", John Wiley and Sons, New York, 1981, 3rd edition; (c) Man Made and Fiber and Textile Dictionary, Celanese Corporation; (d) Fundamentals of Fibre Formation—The Science of Fibre Spinning and Drawing, Adrezij Ziabicki, John Wiley and Sons, London/New York, 1976; and (e) Man Made Fibres, by R. W. Moncrieff, John Wiley and Sons, London/New York, 1975.

Numerous other processes that can be performed before, during and after the spinning and drawing steps. Examples of such processes are disclosed in U.S. Pat. Nos. 4,950,541, 5,082,899, 5,126,199, 5,372,885, 5,456,982, 5,705,565, 2,861,319, 2,931,091, 2,989,798, 3,038,235, 3,081,490, 3,117,362, 3,121,254, 3,188,689, 3,237,245, 3,249,669, 3,457,342, 3,466,703, 3,469,279, 3,500,498, 3,585,685, 3,163,170, 3,692,423, 3,716,317, 3,778,208, 3,787,162, 3,814,561, 3,963,406, 3,992,499, 4,052,146, 4,251,200, 4,350,006, 4,370,114, 4,406,850, 4,445,833, 4,717,325, 4,743,189, 5,162,074, 5,256,050, 5,505,889, 5,582,913, and 6,670,035, all of which are hereby incorporated by reference in their entireties.

In certain embodiments, articles in accordance with the disclosed subject matter can also include, but is not limited to, bicomponent fibers that are partially drawn with varying degrees of draw or stretch, highly drawn bicomponent fibers and mixtures thereof. These can include, for example, a highly drawn polyester core bicomponent fiber with a variety of sheath materials, specifically including a polyethylene sheath such as Trevira T255 (Bobingen, Germany) or a highly drawn polypropylene core bicomponent fiber with a variety of sheath materials, specifically including a polyethylene sheath such as ES FiberVisions AL-Adhesion-C (Varde, Denmark). Additionally, Trevira T265 bicomponent fiber (Bobingen, Germany), having a partially drawn core with a core made of polybutylene terephthalate (PBT) and a sheath made of polyethylene can be used. The use of both partially drawn and highly drawn bicomponent fibers in the same structure can be leveraged to meet specific physical and performance properties based on how they are incorporated into the structure.

Bicomponent fibers that can be used in accordance with embodiments of the disclosed subject matter are not limited in scope to any specific polymers for either the core or the sheath as any partially drawn core bicomponent fiber could provide enhanced performance regarding elongation and strength. The degree to which the partially drawn bicomponent fibers are drawn is not limited in scope as different degrees of drawing will yield different enhancements in performance. The scope of the partially drawn bicomponent fibers encompasses fibers with various core sheath configurations including, but not limited to concentric, eccentric, side by side, islands in a sea, pie segments and other variations. The relative weight percentages of the core and sheath components of the total fiber can be varied. In accordance with embodiments of the disclosed subject matter, partially drawn homopolymers such as polyester, polypropylene, nylon, and other melt spinnable polymers can be used. Multicomponent fibers can have more than two polymers as part of the fiber structure as known in the art.

In particular embodiments, the bicomponent fibers in a particular layer can include from about 0 to about 50 percent by weight of the layer. In certain embodiments, the bicomponent fibers in a particular layer comprise from about 0 to about 30 percent by weight of the layer, from about 0 to about 25 percent by weight of the layer, from about 0 to about 15 percent by weight of the layer, from about 5 to about 40 percent by weight of the layer, from about 5 to about 30 percent by weight of the layer, from about 10 to about 40 percent by weight of the layer, of from about 10 to about 30 percent by weight of the layer. In accordance with other embodiments of the disclosed subject matter, the bicomponent fibers can comprise from about 50 to about 100 percent by weight of the layer, from about 50 to about 75% by weight of the layer, or from about 60 to about 75% by weight of the layer.

Other synthetic fibers suitable for use in various embodiments as monocomponent fibers, components of bicomponent fibers, components of multicomponent fibers, or as binder fibers include, but are not limited to, fibers made from various polymers including, by way of example and not by limitation, acrylic, polyamides (including, but not limited to, Nylon 6, Nylon 6/6, Nylon 12, polyaspartic acid, polyglutamic acid), polyamines, polyimides, polyacrylics (including, but not limited to, polyacrylamide, polyacrylonitrile, esters of methacrylic acid and acrylic acid), polycarbonates (including, but not limited to, polybisphenol A carbonate, polypropylene carbonate), polydienes (including, but not limited to, polybutadiene, polyisoprene, polynorbornene), polyepoxides, polyesters (including, but not limited to, polyethylene terephthalate, polybutylene terephthalate, polytrimethylene terephthalate, polycaprolactone, polyglycolide, polylactide, polyhydroxybutyrate, polyhydroxyvalerate, polyethylene adipate, polybutylene adipate, polypropylene succinate), polyethers (including, but not limited to, polyethylene glycol (polyethylene oxide), polybutylene glycol, polypropylene oxide, polyoxymethylene (paraformaldehyde), polytetramethylene ether (polytetrahydrofuran), polyepichlorohydrin), polyfluorocarbons, formaldehyde polymers (including, but not limited to, urea-formaldehyde, melamine-formaldehyde, phenol formaldehyde), natural polymers (including, but not limited to, cellulosics, chitosans, lignins, waxes), polyolefins (including, but not limited to, polyethylene, polypropylene, polybutylene, polybutene, polyoctene), polyphenylenes (including, but not limited to, polyphenylene oxide, polyphenylene sulfide, polyphenylene ether sulfone), silicon containing polymers (including, but not limited to, polydimethyl siloxane, polycarbomethyl silane), polyurethanes, polyvinyls (including, but not limited to, polyvinyl butyral, polyvinyl alcohol, esters and ethers of polyvinyl alcohol, polyvinyl acetate, polystyrene, polymethylstyrene, polyvinyl chloride, polyvinyl pryrrolidone, polymethyl vinyl ether, polyethyl vinyl ether, polyvinyl methyl ketone), polyacetals, polyarylates, and copolymers (including, but not limited to, polyethylene-co-vinyl acetate, polyethylene-co-acrylic acid, polybutylene terephthalate-co-polyethylene terephthalate, polylauryllactam-block-polytetrahydrofuran), polybuylene succinate and polylactic acid based polymers.

Multicomponent fibers having enhanced reversible thermal properties as described in U.S. Pat. No. 6,855,422, which is hereby incorporated by reference in its entirety, can be used in accordance with certain embodiments of the disclosed subject matter. These multicomponent fibers can contain temperature regulating materials, such as phase change materials that have the ability to absorb or release thermal energy to reduce or eliminate heat flow. A phase change material can include any substance, or mixture of substances, that has the capability of absorbing or releasing thermal energy to reduce or eliminate heat flow at or within a temperature stabilizing range. The temperature stabilizing range can include a particular transition temperature or range of transition temperatures. A phase change material used in conjunction with various embodiments of the disclosed subject matter can inhibit a flow of thermal energy during a time when the phase change material is absorbing or releasing heat, for example as the phase change material undergoes a transition between two states, including, but not limited to, liquid and solid states, liquid and gaseous states, solid and gaseous states, or two solid states. This action can be transient, and can occur until a latent heat of the phase change material is absorbed or released during a heating or cooling process. Thermal energy can be stored or removed from the phase change material, and the phase change material can be effectively recharged by a source of heat or cold. By selecting an appropriate phase change material, the multi-component fiber can be designed for use in any one of numerous products.

Various manufacturing processes of bicomponent and multicomponent fibers, and treatment of such fibers with additives, that can be used in accordance with embodiments of the disclosed subject matter are disclosed in U.S. Pat. Nos. 4,394,485, 4,684,576, 4,950,541, 5,045,401, 5,082,899, 5,126,199, 5,185,199, 5,705,565, 6,855,422, 6,811,871, 6,811,716, 6,838,402, 6,783,854, 6,773,810, 6,846,561, 6,841,245, 6,838,402, and 6,811,873 all of which are hereby incorporated by reference in their entireties. In one embodiment, the ingredients can mixed, melted, cooled, and rechipped. The final chips can then be incorporated into a fiber spinning process to make the desired bicomponent fiber. In certain embodiments, the polymer can be directly melt spun from monomers. The rate of forming or temperatures used in the process are similar to those known in the art, for example similar to the rate of forming or temperatures disclosed in U.S. Pat. No. 4,950,541, which is incorporated by reference herein in its entirety, where maleic acid or maleic compounds are integrated into bicomponent fibers.

In certain non-limiting embodiments of the disclosed subject matter, high strength bicomponent fibers can be used. In accordance with some embodiments of the disclosed subject matter, a minimal amount of synthetic bicomponent fiber can be used in the wiping substrate in order to reduce cost, reduce environmental burden and improve biodegradability performance. Bicomponent fibers that deliver higher strength, especially higher wet strength, can be used at a lower add-on level versus standard bicomponent fiber to help achieve desired performance attributes. These higher strength bicomponent fibers can be used in wipes, including, for example, non-flushable, non-dispersible wipes such as baby wipes, hard surface cleaning wipes or in other products made by the airlaid manufacturing process such as floor cleaning substrates, feminine hygiene substrates and table top substrates or in other technologies with varied end-use applications including, but not limited to nonwoven processes such as but not limited to carding, spunlacing, needlepunching, wetlaid and other various nonwoven, woven and web forming processes.

The strength of a bicomponent fiber can be increased using a number of different approaches or technologies that are known in the art. Such technologies can be used individually and in combination with each other. For example, when a bicomponent fiber has a polyethylene sheath, known technologies, such as incorporating maleic anhydride or other chemically similar additives to the polyethylene sheath, have been shown to increase the bonding strength, as measured by the cross directional wet strength, in an airlaid web. Such bicomponent fibers with a polyethylene sheath can have polyester core, a polypropylene core, a polylactic acid core, a nylon core or any other melt-spinnable polymer with a higher melting point than the polyethylene sheath. Another example is reducing the denier of the bicomponent fiber such that there are more fibers per unit mass, which provides more bonding points in the web. Combining the lower denier technology with the maleic anhydride technology has also been shown to provide a further increase in strength over either of these technologies by themselves.

Continuous Filaments

Nonwoven materials in accordance with the disclosed subject matter can also include continuous filaments. For example, second layer 104 of structure 100 can include continuous filaments. Filaments are fibers that are very long in proportion to their diameter. In accordance with one embodiment of the disclosed subject matter, continuous filaments can be produced by melting and extruding a thermoplastic polymer through fine nozzles, followed by cooling the polymer, for example by an air flow blown at and along the polymer streams, and solidification of the filaments into strands that can be treated by drawing, stretching or crimping. Chemicals to provide additional functions to the filaments can be added to the surface of the filaments. In accordance with other embodiments, filaments can be produced by chemical reaction of a solution of fiber-forming reactants entering a reagence medium, for example by spinning of viscose fibers from a cellulose xanthate solution into sulphuric acid.

Continuous filaments in accordance with the disclosed subject matter can contain cellulose components. For example, the continuous filaments can be regenerated cellulose filaments. Regenerated cellulose filaments include, but are not limited to, viscose, rayon, acetate, lyocell, Tencel®, Modal®, and other filaments known to those skilled in the art. Methods of forming regenerated cellulose filaments are known in the art as described, for example, in U.S. Patent Publication Nos. 2009/025862 and 2009/0312731, which are incorporated by reference herein in their entireties.

Continuous filaments in accordance with the disclosed subject matter can be synthetic filaments. Synthetic filaments can include filaments formed from linear thermoplastic polymers, including polystyrene and polystyrene copolymers, poly(vinyl chloride) and co-polymers of vinyl chloride and vinyl acetate, polyethylene, polypropylene, polyethylene-polypropylene co-polymers, polyamides, polyesters and polyurethane. Both oriented and unoriented filament can be used, and various filament cross sections can be imparted, including without limitation circular, lobular, trifoil, triangular, polygonal, star, X and Y cross sections.

Mixtures of continuous filaments can be employed where the compositions of the filament are compatible with fusing operations, such as heat sealing. Continuous filaments can have suitable crimp imparted to their length or a portion thereof. Filaments can contain organic or inorganic modifications to make them biodegradable or subject to decomposition during or after use.

Meltblown filaments can be produced by extruding molten thermoplastic polymer through fine nozzles in very fine streams and directing converging air flows towards the polymer streams such that they are drawn into continuous filaments of very small diameter. Examples of methods for production of meltblown filaments are described in U.S. Pat. Nos. 3,849,241 and 4,048,364, which are incorporated by reference herein in their entireties. The fibers can be microfibers or macrofibers depending on their dimensions. Microfibers have a diameter of up to 20 µm and usually between 2-12 µm. Macrofibers have a diameter greater than 20 µm, usually 20-100 µm.

In accordance with certain embodiments of the disclosed subject matter, spunbond filaments can be produced in a manner similar to meltblown filaments, but the air flows used are cooler and the stretching of the filaments is performed by air to achieve a desired diameter. The fiber diameter of spunbond filaments is usually above 10 µm, typically from 10-100 µm. Examples of methods for production of spunbond filaments are described in U.S. Pat. Nos. 4,813,864 and 5,545,371, which are incorporated by reference herein in their entireties.

As used herein, the term "spunlaid filaments" refers to spunbond and meltblown filaments because they are directly laid down on a moving surface to form a web that is subsequently bonded. In accordance with certain embodiments of the disclosed subject matter, a thermoplastic polymer that is cohesive enough to be drawn out with airflow as described above can be used for the production of meltblown and spunbond fibers. Examples of suitable polymers include without limitation polyolefines, polyamides, polyesters and polylactides, and copolymers thereof. Natural polymers with thermoplastic properties are also suitable.

Spunbond processes generally produce webs which are oriented in the machine direction. Such webs have high stretch in the machine direction, but continuous filaments generally are not bonded to adjacent filaments because they are cooled in quench air before the web is formed. Therefore, webs produced using spunbond processes generally do not have much cross machine tensile strength or elongation. Meltblown processes, on the other hand, generally produce webs that have higher strength (but lower elongation) in both the machine direction and cross machine direction, because the continuous filaments bond to adjacent continuous filaments before they cool and therefore are constrained from stretching in the cross machine direction.

In accordance with embodiments of the disclosed subject matter, continuous filament webs are partially constrained in the cross machine direction. Such webs can be produced, for example, by using low modulus polymers, low bond area rolls, low bonding temperatures, and similar techniques. Techniques for achieving partial constraint using, for example, spunbond and meltblown processes are known in the art. In accordance with such techniques, for example, a meltblown process can be used which achieves higher filament diameters and creates a more porous structure with less filament to filament bonding. Similarly, a spunbond process can be used that achieves more filament to filament bonding.

In accordance with embodiments of the disclosed subject matter, the continuous filaments can have a thickness of between about 0.001 mm and about 0.02 millimeters. For example, a filament can have a thickness of about 0.001 mm, about 0.002 mm, about 0.004 mm, about 0.006 mm, about 0.008 mm, about 0.01 mm, about 0.012 mm, about 0.014 mm, about 0.016 mm, about 0.018 mm, or about 0.02 mm.

Binders

In accordance with embodiments of the disclosed subject matter, a binder can be used to bind two layers. For example, and with further reference to FIG. 1, a binder can be used to bind first layer 102 to second layer 104.

In another embodiment, first layer 102 and/or second layer 104 can include a binder to create bonds between the fibers and/or continuous filaments within a particular layer.

Suitable binders include, but are not limited to, liquid binders, powder binders, and fiber binders such as bicomponent fibers. Non-limiting examples of liquid binders include emulsions, solutions, and suspensions of binders. Non-limiting examples of binders include polyethylene powders, copolymer binders, vinylacetate ethylene binders, styrene-butadiene binders, urethanes, urethane-based binders, acrylic binders, thermoplastic binders, natural polymer-based binders, and mixtures thereof.

Suitable binders include, but are not limited to, copolymers, vinylacetate ethylene ("VAE") copolymers which can have a stabilizer such as Wacker Vinnapas EF 539, Wacker Vinnapas EP907, Wacker Vinnapas EP129, Celanese Duroset E130, Celanese Dur-O-Set Elite 130 25-1813 and Celanese Dur-O-Set TX-849, Celanese 75-524A, polyvinyl alcohol—polyvinyl acetate blends such as Wacker Vinac 911, vinyl acetate homopolymers, polyvinyl amines such as BASF Luredur, acrylics, cationic acrylamides—polyacrylamides such as Bercon Berstrength 5040 and Bercon Berstrength 5150, hydroxyethyl cellulose, starch such as National Starch CATO RTM 232, National Starch CATO RTM 255, National Starch Optibond, National Starch Optipro, or National Starch OptiPLUS, guar gum, styrene-butadienes, urethanes, urethane-based binders, thermoplastic binders, acrylic binders, and carboxymethyl cellulose such as Hercules Aqualon CMC. In particular embodiments, the binder can be a natural polymer based binder. Non-limiting examples of natural polymer based binders include polymers derived from starch, cellulose, chitin, and other polysaccharides.

In certain embodiments, the binder can be water-soluble. In one embodiment, the binder is a vinylacetate ethylene copolymer. One non-limiting example of such a copolymer is EP907 (Wacker Chemicals, Munich, Germany). Vinnapas EP907 can be applied at a level of about 10% solids incorporating about 0.75% by weight Aerosol OT (Cytec Industries, West Paterson, N.J.), which is an anionic surfactant. Other classes of liquid binders such as styrene-butadiene and acrylic binders can also be used.

In certain embodiments, the binder is not water-soluble. Examples of these binders include, but are not limited to, AirFlex 124 and 192 (Air Products, Allentown, Pa.) having an opacifier and whitener, including but not limited to titanium dioxide. Binders that are not water soluble can be dispersed in an emulsion. Other binders include, but are not limited to, Celanese Emulsions (Bridgewater, N.J.) Elite 22 and Elite 33.

Polymers in the form of powders can also be used as binders. These powders can be thermoplastic or thermoset in nature. The powders can function in a similar manner as the fibers described above. In particular embodiments, polyethylene powder can be used. Polyethylene includes, but is not limited to, high density polyethylene, low density polyethylene, linear low density polyethylene, and other derivatives thereof. Polyethylenes are suitable for certain applications due to their low melting point. These polyethylene powders can have an additive to increase adhesion to cellulose such as a maleic or succinic additive. Other polymers suitable for use in various embodiments as powders, which may or may not contain additives to further enhance their bonding effectiveness, include, by way of example and not limitation, acrylic, polyamides (including, but not limited to, Nylon 6, Nylon 6/6, Nylon 12, polyaspartic acid, polyglutamic acid), polyamines, polyimides, polyacrylics (including, but not limited to, polyacrylamide, polyacrylonitrile, esters of methacrylic acid, and acrylic acid), polycarbonates (including, but not limited to, polybisphenol A carbonate polypropylene carbonate), polydienes (including, but not limited to, polybutadiene, polyisoprene and polynorbomene), polyepoxides, polyesters (including, but not limited to, polyethylene terephthalate, polybutylene terephthalate, polytrimethylene terephthalate, polycaprolactone, polyglycolide, polylactide, polyhydroxybutyrate, polyhydroxyvalerate, polyethylene adipate, polybutylene adipate, and polypropylene succinate), polyethers (including, but not limited to, polyethylene glycol (polyethylene oxide), polybutylene glycol, polypropylene oxide, polyoxymethylene (paraformaldehyde), polytetramethylene ether (polytetrahydrofuran), and polyepichlorohydrin), polyfluorocarbons, formaldehyde polymers (including, but not limited to, urea-formaldehyde, melamine-formaldehyde, and phenol formaldehyde), natural polymers (including, but not limited to, cellulosics, chitosans, lignins, waxes), polyolefins (including, but not limited to, polyethylene, polypropylene, polybutylene, polybutene, and polyoctene), polyphenylenes (including, but not limited to, polyphenylene oxide, polyphenylene sulfide, and polyphenylene ether sulfone), silicon containing polymers (including, but not limited to, polydimethyl siloxane, and polycarbomethyl silane), polyurethanes, polyvinyls (including, but not limited to, polyvinyl butyral, polyvinyl alcohol, esters and ethers of polyvinyl alcohol, polyvinyl acetate, polystyrene, polymethylstyrene, polyvinyl chloride, polyvinyl pryrrolidone, polymethyl vinyl ether, polyethyl vinyl ether, and polyvinyl methyl ketone), polyacetals, polyarylates, and copolymers (including, but not limited to, polyethylene-co-vinyl acetate, polyethylene-co-acrylic acid, polybutylene terephthalate-co-polyethylene terephthalate, polylauryllactam-block-polytetrahydrofuran), polybuylene succinate and polylactic acid based polymers.

In particular embodiments where binders are used in the nonwoven material of the presently disclosed subject matter, binders can be applied in amounts ranging from about 0 to about 30 weight percent based on the total weight of the nonwoven material. In certain embodiments, binders can be applied in amounts ranging from about 2 to about 25 weight percent, and also in other embodiments, from about 3 to about 20 weight percent.

These weight percentages are based on the total weight of the nonwoven material. Binder can be applied to one side or both sides of the nonwoven web, in equal or disproportionate amounts. In a particular embodiment, the binder is applied in amounts of about 6 weight percent to each side of a single layer. In another embodiment, the binder is applied to a single side of a patricular layer.

The materials of the presently disclosed subject matter can also include additional additives including, but not limited to, ultra white additives, colorants, opacity enhancers, delustrants and brighteners, and other additives to increase optical aesthetics as disclosed, for example, in U.S. Patent Publication No. 20040121135 published Jun. 24, 2004, which is hereby incorporated by reference in its entirety.

In certain embodiments, the binder can be a thermoplastic binder. Thermoplastic binders include, for example, any thermoplastic polymer which can be melted at temperatures which will not extensively damage the cellulosic fibers. In one embodiment, the melting point of the thermoplastic binding material can be less than about 175° C. Examples of suitable thermoplastic materials include, but are not limited to, suspensions of thermoplastic binders and thermoplastic powders. In particular, the thermoplastic binding material can be, for example, polyethylene, polypropylene, polyvinylchloride, and/or polyvinylidene chloride.

Binders can be applied using any techniques known in the art, including but not limited to spray techniques, foam techniques, and printing techniques.

Functional Additives

One or more layers of the multilayer structure can contain functional additives. Functional additives can include particles, flakes, powders, granules and the like which serve as absorbents, odor control agents (such as, for example, zeolites or calcium carbonates, bicarbonates, such as sodium bicarbonate, or fragrances), microbial agents, fire retardant agents, and the like. The particles can include any functional powder or other particle having a particle diameter up to about 3,000 microns.

For example, the functional additive can be a superabsorbent particle (SAP). SAPs include particles, flakes, powders, granules, and the like which server as absorbents. In one embodiment of this disclosed subject matter, a nonwoven material can contain from about 0 to about 80 percent by weight of SAP, from about 0 to about 50 percent by weight of SAP, from about 0 to about 30 percent by weight SAP, from about 10 to about 50 percent by weight of SAP, or from about 10 to about 30 percent by weight of SAP.

In accordance with embodiments of the disclosed subject matter, the functional particles used in the core can include superabsorbent polymer particles (also known as superabsorbent polymers). The term "superabsorbent polymer" refers to a normally water-soluble polymer, which has been cross-linked. Superabsorbent polymers which can be used in accordance with the disclosed subject matter include, for example: SAPs in their particulate form such as irregular granules, spherical particles, staple fibers and other elongated particles. U.S. Pat. Nos. 5,147,343; 5,378,528; 5,795,439; 5,807,916; and 5,849,211, which are incorporated by reference herein in their entireties, describe exemplary superabsorbent polymers and methods of making superabsorbent polymers.

Methods of making water-soluble polymers such as carboxylic polyelectrolytes to create hydrogel-forming materials are known in the art. Methods of crosslinking carboxylated polyelectrolytes to obtain superabsorbent polymers are also known in the art. SAP particles useful in the practice of this disclosed subject matter are commercially available from a number of manufacturers, including Dow Chemical (Midland, Mich.), Stockhausen (Greensboro, N.C.), and Chemdal (Arlington Heights, Ill.). One conventional granular superabsorbent polymer is based on poly(acrylic acid) which has been crosslinked during polymerization with any of a number of multi-functional co-monomer crosslinking agents, as is well known in the art. Examples of multifunctional crosslinking agents are set forth in U.S. Pat. Nos. 2,929,154; 3,224,986; 3,332,909; and 4,076,673, all of which are hereby incorporated by reference in their entireties. Other water-soluble polyelectrolyte polymers are known to be useful for the preparation of superabsorbents by crosslinking; these polymers include carboxymethyl starch, carboxymethyl cellulose, chitosan salts, gelatin salts, etc. Such other polyelectrolyte polymers are not, however, commonly used on a commercial scale to enhance absorbency of disposable absorbent articles, primarily due to lower absorbent efficiency or higher cost. Superabsorbent particulate polymers are also described in detail in U.S. Pat. Nos. 4,102,340 and RE32,649, both of which are hereby incorporated by reference. Suitable SAPs yield high gel volumes or high gel strength as measured by the shear modulus of the hydrogel. Such SAPs contain relatively low levels of polymeric materials that can be extracted by contact with synthetic urine (so-called "extractables"). SAPs are well known and are commercially available from several sources. One example is a starch graft polyacrylate hydrogel marketed under the name IM1000 (BASF; Portsmouth, Va.). Other commercially available SAPs are marketed under the trademark SANWET (Sanyo Kasei Kogyo; Kabushild, Japan), SUMIKA GEL (Sumitomo Kagaku Kabushiki; Haishi, Japan), FAVOR (Stockhausen; Garyville, La.) and the ASAP series (BASF; Aberdeen, Miss.). In certain embodiments for use with the presently disclosed subject matter, SAPs are polyacrylate-based. As used in the disclosed subject matter, SAP particles of any size or shape suitable for use in an absorbent core can be employed.

Functional additives can also include odor control agents including, but not limited to, zeolites, dextrin-based additives, baking soda, and microcapsules that release fragrances. Microbial control agents can include antimicrobial and microbiostatic agents in powder or microcapsule form. Additional functional additives can be used as known in the art for their intended purpose.

Surface treatments for improving wettability can also be used in accordance with embodiments of the disclosed subject matter. Any surface treatment known in the art for improving wettability can be applied, including surfactants such as non-ionic surfactants (e.g., octylphenoxypolyethoxy ethanol), organosilicones, polyethylene oxides, and primary and secondary alcohols. Exemplary surface treatments are described in U.S. Patent Publication No. 2006/0292951, which is incorporated by reference herein in its entirety.

Nonwoven Material

The disclosed subject matter includes a multilayer nonwoven material. The nonwoven material can include one, or two or more layers. In certain embodiments, the nonwoven material can include three or more layers. In other embodiments, the nonwoven material can include four or more layers.

In certain embodiments, the layers can be bonded on at least a portion of at least one of their outer surfaces with binder. Binding can include, but is not limited to, the binder chemically binding with a portion of the layer, as long as the binder can remain associated in close proximity with the layer, by coating, adhering, precipitation, or any other mechanism such that it is not dislodged from the layer during normal handling of the layer. For convenience, the association between the layer and the binder discussed above can be referred to as the bond between layers, and the binder can be said to be bonded to the layer.

With reference to FIG. 2, multilayer materials in accordance with various embodiments of the disclosed subject matter are shown.

Figure 2B:
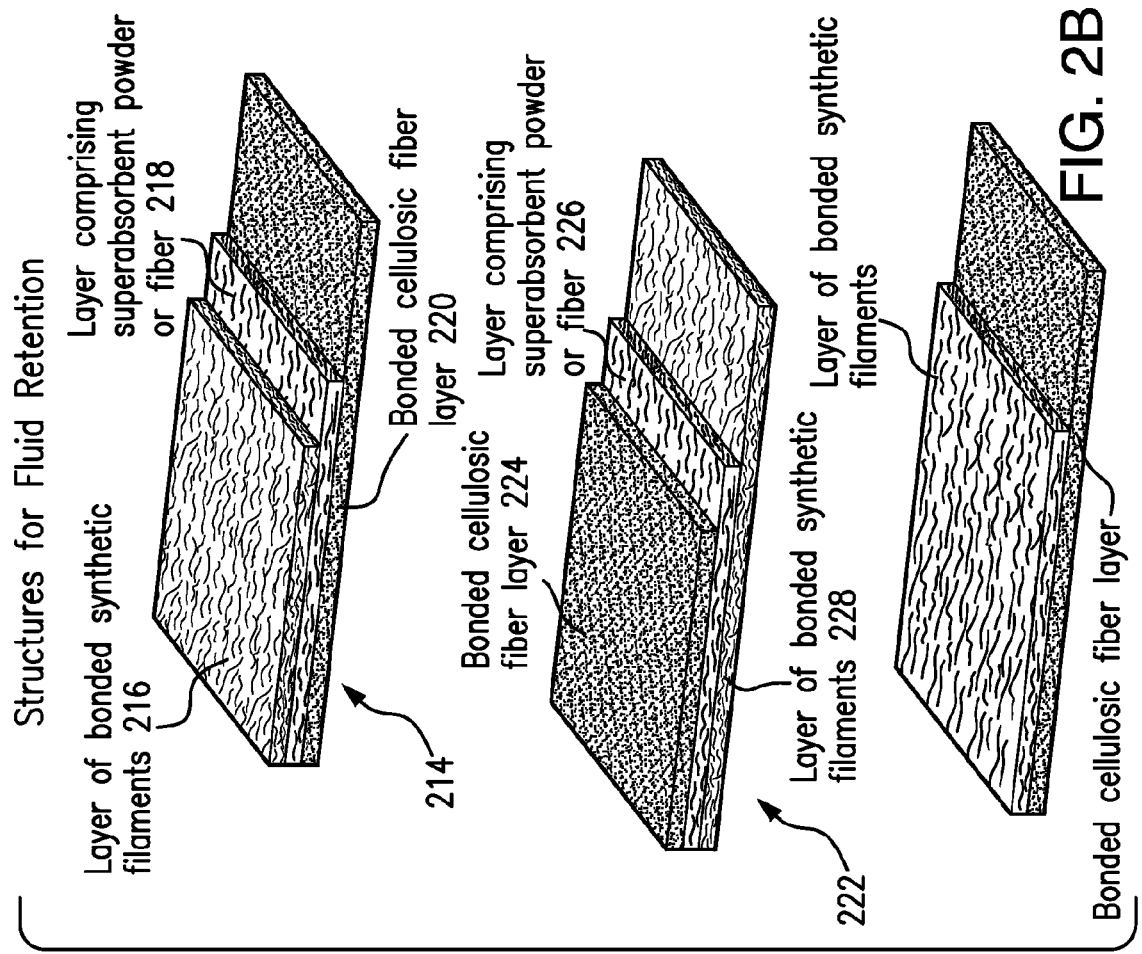
Figure 2A:
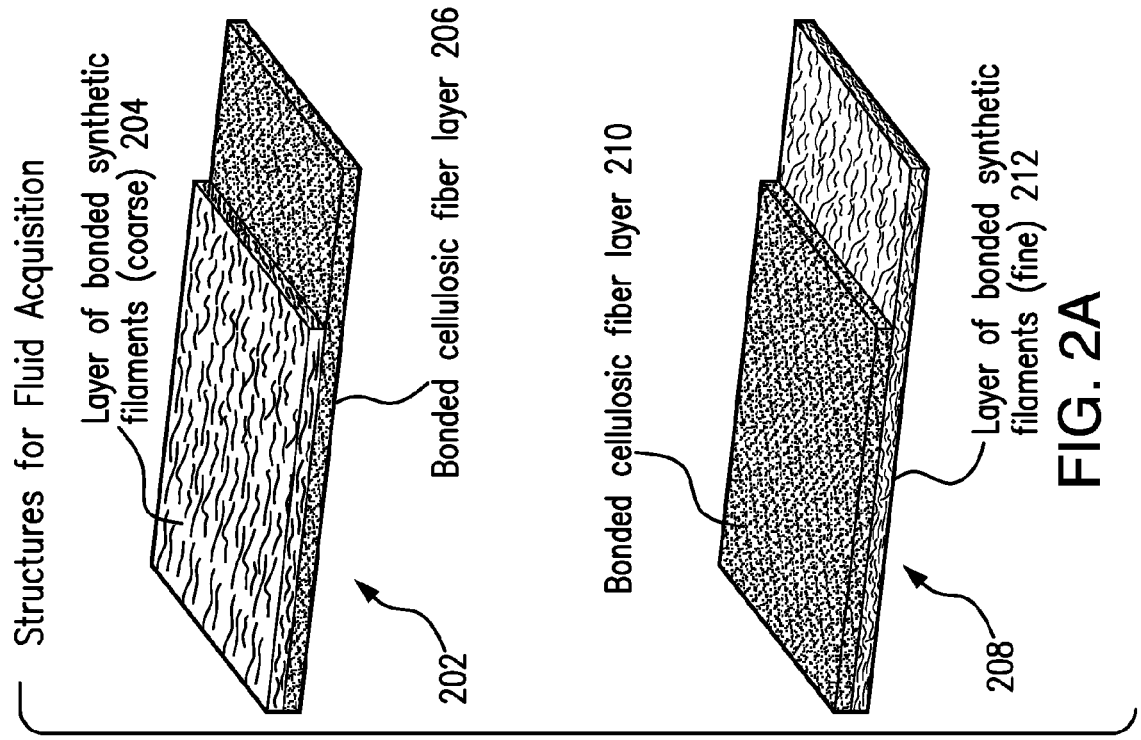

In certain embodiments, the nonwoven material can include two layers. With reference to FIG. 2A, examples of two layer structures in accordance with the disclosed subject matter are shown. Structure 202 includes a first layer 204 containing bonded continuous filaments and a second layer 206 containing bonded fibers. The continuous filaments in first layer 204 can be, for example, synthetic filaments. In accordance with certain embodiments of the disclosed subject matter, the continuous filaments can be coarse filaments in order to form a gradient to enhance fluid flow. The fibers in second layer 206 can be, for example, cellulosic fibers or synthetic fibers such as bicomponent fibers. FIG. 2A further illustrates a two layer structure 208 in accordance with another embodiment of the disclosed subject matter. Structure 208 includes a first layer 210 containing bonded fibers and a second layer 212 containing bonded continuous filaments. The fibers in first layer 210 can be, for example, cellulosic fibers or synthetic fibers such as bicomponent fibers. The continuous filaments in second layer 212 can be, for example, synthetic fibers. In accordance with certain embodiments of the disclosed subject matter, the continuous filaments can be fine filaments in order to form a gradient to enhance fluid flow.

In certain embodiments, the nonwoven material can include three layers. With reference to FIGS. 2B and 2C, examples of three layer structures in accordance with the disclosed subject matter are shown. In accordance with an exemplary three-layer structure 214 shown in FIG. 2B, the material includes a first layer 216 containing bonded continuous filaments, a second layer 218 containing a superabsorbent material such superabsorbent particles, superabsorbent powder, superabsorbent fiber, and the like, and a third layer 220 containing bonded fibers. The continuous filaments in first layer 216 can be, for example, synthetic filaments. The fibers in the third layer 220 can be, for example, cellulosic fibers or synthetic fibers such as bicomponent fibers.

With further reference to FIG. 2B, a three-layer structure 222 in accordance with the disclosed subject matter can include a first layer 224 containing bonded fibers, a second layer 226 containing a superabsorbent material such superabsorbent particles, superabsorbent powder, superabsorbent fiber, and the like, and a third layer 228 containing continuous filaments.

A three layer structure 230 in accordance with other embodiments of the disclosed subject matter is shown in FIG. 2C. Structure 230 can include two outer layers 232, 236 of bonded fibers and a middle layer 234 of bonded continuous filaments. The fibers in first layer 232 can be cellulosic fibers, synthetic fibers, or a mixture thereof. In certain embodiments, the first layer 232 can be coated with binder on its outer surface. The continuous filaments in middle layer 234 can be, for example, synthetic filaments. In certain embodiments, the middle layer 234 can be coated on its top and bottom surfaces with binder that has penetrated the first layer 232 and third layer 236. In accordance with embodiments of the disclosed subject matter, the binder can further have penetrated throughout the middle layer 234, depending on the need for binder penetration. The fibers in third layer 236 can include cellulosic fibers, synthetic fibers, or a mixture thereof. The fibers in first layer 232 can be the same as or different than the fibers in third layer 236.

The characteristics of the multilayer material can depend on many factors. For example, the basis weight ranges for the various layers can depend on factors including, but not limited to, the end use application, desired properties, number of layers, raw materials, layer forming technology, adhesive parameters, and the like. For example, an exemplary feminine hygiene acquisition layer in accordance with the disclosed subject matter can have a basis weight between about 60 gsm and about 100 gsm. An exemplary absorbent core, which can include superabsorbent particles such as supersabsorbent polymer particles, can have a basis weight between about 100 gsm and about 250 gsm, depending on the product application. The basis weight of an absorbent core for a sanitary napkin, for example, can be very different than the basis weight of an absorbent core for a pantiliner. The composition of the multilayer structure can also differ based on the application. A exemplary multilayer structure for use as an adult care absorbent pad in accordance with the disclosed subject matter can be a two layer nonwoven material as depicted, for example, in FIG. 2A. The two layer structure can have a basis weight of between about 300 gsm and about 500 gsm, and can have a continuous filament layer comprising between about 2% and about 5% of the structure by weight and a cellulosic fiber layer comprising between about 95% and about 98% of the structure by weight. As another example, a multilayer structure for use as an adult care absorbent layer can be a two layer nonwoven material having a basis weight of between about 80 gsm and about 150 gms. The structure can include a continuous filament layer comprising between about 5% and about 20% of the structure by weight and a cellulosic fiber layer comprising between about 80% and about 95% of the structure by weight. A person having ordinary skill will understand that these examples are provided for explanation and not limitation, and that the basis weight, relative composition by weight, and other parameters of multilayer structures in accordance with the disclosed subject matter can vary based on numerous factors as previously described.

The amount of the materials in each layer can vary. In accordance with certain embodiments of the disclosed subject matter, layers containing fibers can include from about 70 to about 100 weight percent fibers and from about 0 to about 30 weight percent binder. Layers containing continuous filaments can include from about 70 to about 100 weight percent continuous filaments. For purposes of explanation and not limitation, and with further reference to FIG. 2C, the first layer 232 can include from about 70 to about 100 weight percent fibers and from about 0 to about 30 weight percent binder; the second layer 234 can include from about 70 to about 100 weight percent continuous filaments; and the third layer 236 can include from about 70 to about 100 weight percent fibers and from about 0 to about 30 weight percent binder.

In certain embodiments of the disclosed subject matter, at least a portion of at least one outer layer can be coated with binder. In particular embodiments of the disclosed subject matter, at least a portion of each outer layer can be coated with binder.

In certain embodiments, the nonwoven material can include at least four layers, where at least one or more layer is repeated adjacent to another layer of the same or different configuration. In still other embodiments, the multilayer nonwoven material can include five, or six, or more than six layers.

In particular embodiments of the disclosed subject matter, at least part of at least one outer layer can be coated with binder at least in part. In particular embodiments, the binder can be from about 0 to about 30 weight percent based on the total weight of the nonwoven material. In certain embodiments, the binder can be from about 2 to about 25 weight percent, or from about 3 to about 20 weight percent.

In accordance with embodiments of the disclosed subject matter, the nonwoven material can have a basis weight of from about 30 gsm to about 500 gsm. For example, the nonwoven material can have a basis weight of from about 30 gsm to about 80 gsm, from about 100 to about 300 gsm, or from about 40 to about 100 gsm. For example, the nonwoven material can have a basis weight of about 30 gsm, about 40 gsm, about 50 gsm, about 60 gsm, about 70 gsm, about 80 gsm, about 90 gsm, about 100 gsm, about 150 gsm, about 200 gsm, about 250 gsm, about 300 gsm, about 400 gsm, or about 500 gsm.

In accordance with embodiments of the disclosed subject matter, the nonwoven material can have a density of about 0.03 g/cc to about 0.15 g/cc. For example, the nonwoven material can have a density of about 0.03 g/cc, about 0.05 g/cc, about 0.07 g/cc, about 0.09 g/cc, about 0.11 g/cc, about 0.13 g/cc, or about 0.15 g/cc.

The caliper of the nonwoven material refers to the caliper of the entire nonwoven material. In accordance with embodiments of the disclosed subject matter, the caliper of the nonwoven material can be about 0.5 mm to about 5.0 mm. For example, the caliper of the nonwoven material can be about 0.5 mm to about 3.0 mm, or about 0.5 mm to about 1.5 mm.

In accordance with embodiments of the disclosed subject matter, the multilayer structures can have elongation at peak load that is less than half of total elongation, as shown in a stress-strain curve. For example, the multilayer structures can have elongation at peak load that is less than about 45% of total elongation, less than about 40% of total elongation, less than about 35% of total elongation, less than about one third of total elongation, less than about 30% of total elongation, less than about 25% of total elongation, or less than about 20% of total elongation.

Methods of Making Nonwoven Materials

Exemplary materials, structures and manufacturing processes that can be used in the practice of this disclosed subject matter are disclosed in U.S. Pat. Nos. 6,241,713; 6,353,148; 6,353,148; 6,171,441; 6,159,335; 5,695,486; 6,344,109; 5,068,079; 5,269,049; 5,693,162; 5,922,163; 6,007,653; 6,420,626; 6,355,079; 6,403,857; 6,479,415; 6,495,734; 6,562,742; 6,562,743; and 6,559,081; U.S. Publication No. 20030208175; U.S. Publication No. 20020013560, and U.S. patent application Ser. No. 09/719,338 filed Jan. 17, 2001; all of which are hereby incorporated by reference in their entireties.

A variety of processes can be used to assemble the materials used in the practice of this disclosed subject matter to produce the materials of this disclosed subject matter, including but not limited to, traditional wet laying process or dry forming processes such as airlaying and carding or other forming technologies such as spunlace or airlace. For example, an exemplary process for hydroentangling wood pulp into a continuous filament web is described in U.S. Pat. No. 5,284,703. An exemplary process for hydroentangling wood pulp into a carded web is described in U.S. Pat. No. 4,442,161. An exemplary process for manufacturing a patterned hydroentangled product is described in U.S. Pat. No. 3,485,706. An exemplary wet laying process for hydroentangling short plant fibers is described in U.S. Pat. No. 5,958,186. Exemplary processes for manufacturing meltblown and coform materials are described in U.S. Pat. Nos. 3,849,241, 4,100,324, 4,469,734, 4,818,464, and 5,350,624. Exemplary spunbond processes are described in U.S. Pat. Nos. 4,340,563, 4,692,618, and 5,382,400. Each of these patents are incorporated by reference herein in their entireties. These processes and other processes known in the art can be used in accordance with various embodiments of the disclosed subject matter.

In certain embodiments, the materials can be prepared by airlaid processes. Airlaid processes include, but are not limited to, the use of one or more forming heads to deposit raw materials of differing compositions in selected order in the manufacturing process to produce a product with distinct strata. This allows great versatility in the variety of products which can be produced in accordance with the disclose subject matter. Exemplary airlaid processes are described in U.S. Pat. Nos. 4,014,635 and 4,640,810, which are incorporated by reference herein in their entireties.

In one embodiment, the nonwoven material can be prepared as a continuous airlaid web. The airlaid web can be prepared by disintegrating or defiberizing a cellulose pulp sheet or sheets, for example by hammermill, to provide individualized fibers. Rather than a pulp sheet of virgin fiber, the hammermills or other disintegrators can be fed with recycled airlaid edge trimmings and off-specification transitional material produced during grade changes and other airlaid production waste. In accordance with certain embodiments, production waste can be recycled, which improves the economics of the process. The individualized fibers from whichever source, virgin or recycled, can be air conveyed to forming heads on the airlaid web-forming machine. A number of manufacturers make airlaid web forming machines that can be used in accordance with the disclosed subject matter, including Dan-Web Forming of Aarhus, Denmark, M&J Fibretech A/S of Horsens, Denmark, Rando Machine Corporation, Macedon, N.Y. which is described in U.S. Pat. No. 3,972,092, Margasa Textile Machinery of Cerdanyola del Valles, Spain, and DOA International of Wels, Austria. For example, the machine described in U.S. Pat. No. 3,972,092, which is incorporated herein by reference in its entirety, can be used. Airlaid web forming machines using spike forming processes, such as the devices available from Formfiber Denmark ApS (Skovby (Galten), Denmark) or described, for example, in U.S. Pat. No. 7,491,354, which is incorporated by reference herein in its entirety, can also be used. Although particular devices have been identified, a person of skill in the art will understand that forming machines using various methods for opening the fiber and air-conveying to the forming wire can be used to produce webs in accordance with the disclosed subject matter.

Dan-Web forming heads can include rotating or agitated perforated drums, which serve to maintain fiber separation until the fibers are pulled by vacuum onto a foraminous forming conveyor or forming wire. In certain M&J machines, the forming head is basically a rotary agitator above a screen. The rotary agitator can include a series or cluster of rotating propellers or fan blades. Other fibers, such as a synthetic thermoplastic fibers, can be opened, weighed, and mixed in a fiber dosing system such as a textile feeder supplied by Laroche S. A. of Cours-La Ville, France. From the textile feeder, the fibers can be air conveyed to the forming heads of the airlaid machine where they are further mixed with the comminuted cellulose pulp fibers from the hammer mills and deposited on the continuously moving forming wire. Where defined layers are desired, separate forming heads can be used for each type of fiber.

The airlaid web can be transferred from the forming wire to a calendar or other densification stage to densify the web, if necessary, to increase its strength and control web thickness. In one embodiment, the fibers of the web are then bonded by passage through an oven set to a temperature high enough to fuse the included thermoplastic or other binder materials. In a further embodiment, secondary binding from the drying or curing of a latex spray or foam application occurs in the same oven. The oven can be a conventional through-air oven, can be operated as a convection oven, or can achieve the necessary heating by infrared or even microwave irradiation. In particular embodiments, the airlaid web can be treated with additional additives before or after heat curing.

Techniques for wetlaying cellulosic fibrous material to form sheets such as dry lap and paper are known in the art. Wetlaying techniques include, but are not limited to, handsheeting, and wetlaying with the utilization of paper making machines as disclosed, for instance, by L. H. Sanford et al. in U.S. Pat. No. 3,301,746, which is hereby incorporated by reference in its entirety.

In one embodiment, the fibers that faun the individual layers are allowed to soak overnight in room temperature tap water. The fibers of each individual layer can then slurried. A Tappi disintegrator can be used for slurrying. In particular embodiments, the Tappi disintegrator is use for from about 15 to about 40 counts. The fibers can then be added to a wetlaid handsheet former handsheet basin and the water can be evacuated through a screen at the bottom forming the handsheet. In a particular embodiment, the handsheet basin is a Buckeye Wetlaid Handsheet Former handsheet basin. This individual stratum, while still on the screen, is then removed from the handsheet basin. Multiple strata can be formed in this process.

In certain embodiments, wetlaid webs can be made by depositing an aqueous slurry of fibers on to a foraminous forming wire, dewatering the wetlaid slurry to form a wet web, and drying the wet web. Deposition of the slurry can be accomplished using an apparatus known in the art as a headbox. The headbox has an opening, known as a slice, for delivering the aqueous slurry of fibers onto the foraminous forming wire. The forming wire can be of any suitable construction and mesh size used for dry lap or other paper making processing. Conventional designs of headboxes known in the art for drylap and tissue sheet formation can be used. Suitable commercially available headboxes include, but are not limited to, open, fixed roof, twin wire, inclined wire, and drum former headboxes. Machines with multiple headboxes can be used for making wetlaid multilayer structures.

Once formed, the wet web is dewatered and dried. Dewatering can be performed with foils, suction boxes, other vacuum devices, wet-pressing, or gravitational flow. After dewatering, the web can be transferred from the forming wire to a drying fabric which transports the web to drying apparatuses.

Drying of the wet web can be accomplished utilizing drying techniques known in the art. Drying can be accomplished using, for example, a thermal blow-through dryer, a thermal air-impingement dryer, or heated drum dryers, including Yankee type dryers.

Processes and equipment useful for the production of the nonwoven material of this disclosed subject matter are known in the art and are disclosed in U.S. Pat. Nos. 4,335,066; 4,732,552; 4,375,448; 4,366,111; 4,375,447; 4,640,810; 206,632; 2,543,870; 2,588,533; 5,234,550; 4,351,793; 4,264,289; 4,666,390; 4,582,666; 5,076,774; 874,418; 5,566,611; 6,284,145; 6,363,580; 6,726,461, all of which are hereby incorporated by reference in their entireties.

In one embodiment of this disclosed subject matter, a structure can be formed with one to six forming heads to produce material with one or more strata. The forming heads can be set according to the specific target material by adding matrix fibers to the production line. The matrix fibers added to each forming head can vary depending on target material, where the matrix fibers can be cellulosic, synthetic, or a combination of cellulosic and synthetic fibers.

The forming heads form the multistrata web which is compacted by a compaction roll. In one embodiment, the web can be sprayed with binder on one surface, cured, sprayed with binder on another surface, and then can be cured. The web can then be cured at temperatures between approximately 130° C. and 200° C., and wound and collected at a machine speed of approximately 10 meters per minute to approximately 500 meters per minute.

In a particular embodiment of the presently disclosed subject matter, an airlaid former can be used. This type of former uses air for the conveyance and distribution of individualized fibers on a permeable, continuous forming belt. Nonlimiting examples of such forming technology are the drum (Danweb/ANPAP) or flat screen (Kroyer/M&J) airlaid formers. Fibers can be individualized and air-conveyed to the process by several means. For example, a hammer mill, a textile fiber feeder, and other means known in the art can be used. Fibers suitable for airlaid forming in accordance with certain embodiments of the disclosed subject matter can include, but are not limited to, fluff pulp, bicomponent fibers, monocomponent fibers, or regenerated cellulose such as Rayon or Tencel®.

In a particular embodiment of the presently disclosed subject matter, a meltspun former can be used. Examples of this technology are meltblown or spunbond formers. Nonlimiting suppliers of meltspun technology include Biax-Fiberflim (Greenville, Wis.) and Reifenhauser, Inc. (Davers, Mass.). Raw materials can be synthetic, including for example polypropylene, or can be bio-based, including for example poly lactic acid. Both monocomponent and bicomponent meltspun fibers can be produced. In accordance with one embodiment of the disclosed subject matter, the meltspun web can also be deposited on a permeable forming belt.

In particular embodiments of the disclosed subject matter, embossers can be used throughout the process. Embossers can be smooth or patterned rolls (normally heated) pressing into the formed web to impart aesthetic as well as application-specific properties to the finished web. These properties include but are not limited to caliper, drape, absorbency, emboss pattern. As used herein, the term "embosser" includes calenders, compaction rolls, and similar devices for applying pressure to the web to densify and/or apply a pattern.

In specific embodiments of the disclosed subject matter, binder spray can be applied at various points of the process. The application of binder spray can include depositing a thermosetting binder uniformly on the surface of the web via spray. The binder can be an emulsion of a binder polymer (e.g., synthetic polymer) particles dispersed in water. Binder polymers include but are not limited to vinyl-acetate/ethylene copolymers, urethanes, poly vinyl alcohol, styrene/butadiene, etc. Upon drying and curing, the binder can bond the individualized fibers to each other and to the meltspun web. The dryers allow for heating of the web for the removal of water and the curing of the thermosetting binder to bond the web components together. Examples of drying technology include but are not limited to through-air, infrared, microwave, and steam cans.

Applications

In one aspect of the disclosed subject matter, the nonwoven material can be used as component of a wide variety of absorbent structures, including but not limited to moist toilet tissue, wipes, diapers, feminine hygiene products, incontinent products (including adult incontinence products), cleaning products, and associated materials.

The multilayer structures in accordance with the disclosed subject matter can be used for any application known in the art. For example, the multilayer structures can be used in paper products including bags, tags, toweling, tissue, map papers, paper patterns, napkins, poster papers, filter papers, and in many other grades or uses of paper. The multilayer structures can also be used in disposable absorbent products such as diaper liners, diaper wrap sheets, diaper absorbent structures, feminine napkin wrap sheets, disposable hospital bed pads, and the like. The multilayer structures can also be used in the textile industry for manufacturing upholstery, curtains, blankets, and clothing. The multilayer structure can also be used for food packaging.

The multilayer structures can also be incorporated into a thermoplastic product. The thermoplastics can be used to form automotive parts, office furniture, household goods and kitchenware, appliances, industrial goods, and consumer personal goods.

In accordance with embodiments of the disclosed subject matter, the multilayer material can be used as a filtering media. For example, the multilayer material can be used in an air filter for commercial or residential applications. Other filtration applications include pulse clean and non-pulse cleaned filters for dust collection, gas turbines and engine air intake or induction systems, heavy duty engine intake or induction systems, light vehicle engine intake or induction systems, Z filters, vehicle cabin air filters, off road vehicle cabin air filters, disk drive air filters, photocopier-toner removal, and other filtration application as known in the art.

EXAMPLES

The following examples are merely illustrative of the presently disclosed subject matter and they should not be considered as limiting the scope of the disclosed subject matter in any way.

Example 1: Nonwoven Wipe Material

A nonwoven wipe material according to the presently disclosed subject matter was prepared as Sample 1. Specifically, a nonlimiting example of a wipe material was made following the process depicted in FIG. 3.

Figure 3:
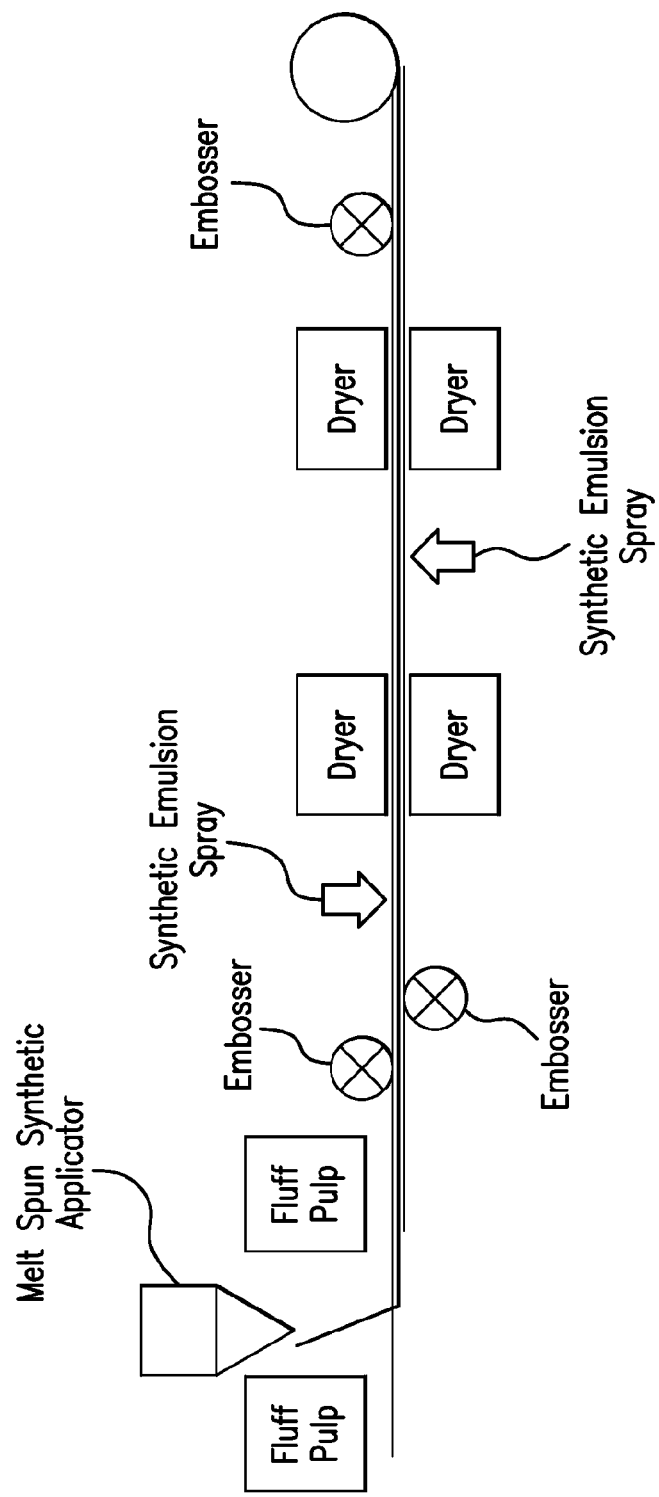
FIG. 3 depicts a nonlimiting process schematic for manufacturing the nonwoven material of the presently disclosed subject matter.

In the current Example, fluff pulp was used to prepare Sample 1. As shown in FIG. 3, two airlaid forming units were used in the process to convey and distribute the individualized fibers onto the permeable, continuous forming belt. The forming technology used in this process was a drum (Danweb/ANPAP). The fibers were individualized by a hammer mill.

A meltspun meltblown former was also used in this process. The supplier for the meltspun technology was Biax-Fiberfilm. The raw materials used were synthetic polypropylene. The meltspun web was also deposited on a permeable forming belt.

As noted in FIG. 3, a layer of fluff pulp was deposited on the belt, followed by meltblown synthetic filaments, and then an additional layer of fluff pulp. Two heated smooth embossers pressed the layers into the formed web to impart aesthetic as well as application-specific properties to the finished web.

A binder spray was then used by depositing a thermosetting binder uniformly on the surface of the web via spray. The binder used was vinyl-acetate/ethylene copolymer. The binder was an emulsion of synthetic polymer particles dispersed in water.

The material then passed through two dryers for drying and curing, where the binder bonded the individualized fibers to each other and to the meltspun web. A second binder spray was utilized from below the forming wire. The material then passed through two additional through-air dryers, which heated the web for the removal of water and the curing of the thermosetting binder to bond the web components together.

The material was then subjected to an embosser, and was then collected in roll form.

The following Table outlines the material used and the composition of the three layer structure of Sample 1.

TABLE 1

Bill of materials

Buckeye FFT-AS pulp
Wacker Vinnapas 192 binder
Polypropylene meltblown scrim produced offline at Biax-Fiberfilm

| Product design | | |
|---|---|---|
| | gsm | % |
| Top layer | | |
| Binder | 3.5 | 5.8 |
| Pulp | 20.5 | 34.2 |
| Middle layer | | |
| Scrim | 12 | 20 |

TABLE 1-continued

| Bottom layer | | |
|---|---|---|
| Pulp | 20.5 | 34.2 |
| Binder | 3.5 | 5.8 |
| Total | 60 | 100 |

Example 2: Nonwoven Feminine Hygiene Material

Sample 2, which is an exemplary three-layer nonwoven structure in accordance with the disclosed subject matter, can be formed using a pilot drum-forming machine using the process shown in FIG. 3. The process and materials are described in Example 1. The structure of Sample 2 is similar to the structure shown in FIG. 2C.

The top and bottom layers of the three-layer nonwoven structure of Sample 2 include cellulose pulp (FFT-AS, Buckeye Technologies Inc.), which were bonded with a polymeric binder in the form of emulsion (Vinnapas 192, Wacker). The basis weights of the top and bottom layers are each 20.5 gsm. The top and bottom layers each include 14.6% Vinnapas 192 binder based on dry weight. The middle layer includes polypropylene meltblown scrim (e.g., from Biax-Fiberfilm), and has a basis weight of 12 gsm.

Table 2 shows exemplary physical characteristics of the exemplary nonwoven structure of Sample 2 and of a latex-bonded airlaid acquisition layer, which can be utilized as a component of the absorbent system in a commercial sanitary napkin product (for example, Casino Ultra Normal). The values shown in Table 2 correspond to data obtained according to the harmonized standard EDANA/INDA test methods.

As shown in Table 2, both nonwoven materials have similar basis weight, caliper and tensile strength, and Sample 2 has more than 100% higher elongation than the commercial material. High elongation can provide improved elasticity, comfort and seal between the personal hygiene article and the skin of the user.

TABLE 2

| Characteristics | Sample 2 | Commercial Acquisition Layer |
|---|---|---|
| Basis Weight (gsm) | 62 | 60 |
| Caliper (mm) | 0.72 | 0.76 |
| MDD (G/in) | 705 | 847 |
| MDDE (%) | 22 | 10 |
| CDD (G/in) | 449 | 598 |
| CDDE (%) | 27 | 12 |
| MDW (G/in) | 534 | 498 |
| MDWE (%) | 26 | — |
| CDW (G/in) | 299 | 299 |
| CDWE (%) | 31 | — |

Sample 2 and the commercial acquisition layer were also compared for their liquid acquisition characteristics. The acquisition tests were performed as follows. The commercial sanitary napkin products were partially disassembled to remove the acquisition layer, leaving remaining components, including the absorbent core, intact. A portion of these partially disassembled products were re-assembled by inserting the original acquisition layers into the structure and placing these layers in the original position. Another portion of partially disassembled sanitary napkins were re-assembled by inserting therein the exemplary three-layer nonwoven structure, previously cut into the shape of the original acquisition layer. The re-assembled product was pressed using an 8.190 kG plate for 1 minute. The prepared composites were tested for their liquid acquisition performance.

The liquid used for the tests, which will be called here synthetic blood, was prepared as follows. In a 1000 mL beaker, about 600 mL of deionized water was used to dissolve 1.00 g of carboxymethylcellulose sodium salt (CMC) (from VWR's U.S. supplier, Spectrum Chemical). The viscosity of a 2% solution of the CMC at 25° C. was 408.4 cps. After the CMC dissolved, 32.5 g of bovine serum albumin (BSA) lyophilized powder, standard grade, having pH 7.0 (from Lampire Biological Labs), was added. 3.05 g of NaCl, 1.15 g of NaHCO$_3$, and 0.15 g of CaCl$_2$ were added to a separate beaker containing a small quantity of deionized water, and the salts were dissolved. The salt solution was added to the larger beaker containing the BSA and the CMC and was mixed. 3 drops of red food color were added, and the solution was poured into the volumetric flask and diluted to 500 mL.

Figure 4:
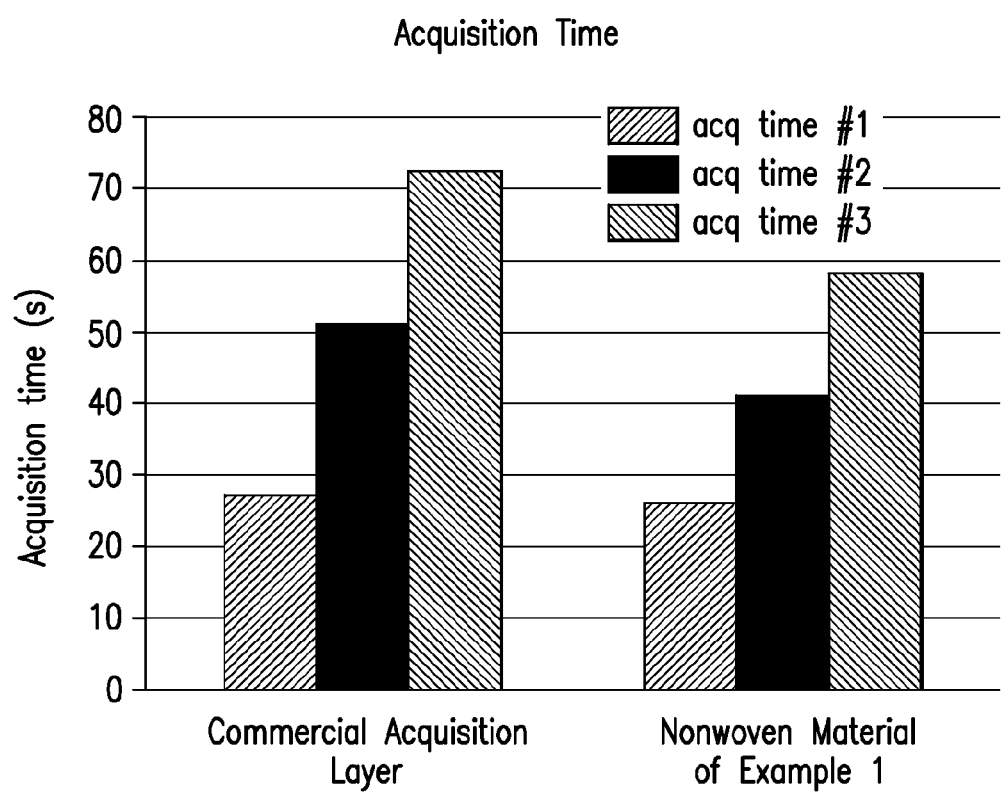
FIG. 4 illustrates improved acquisition performance of the exemplary three-layer nonwoven material.

Each re-assembled product was insulted with 4 mL of the synthetic blood at a rate of 10 mL/min using a small pump. Three acquisition times, #1, #2 and #3, were measured. The interval time between the insults was 10 min. FIG. 4 illustrates improved acquisition performance of Sample 2, with increased improvement at the second and third insult.

Example 3: Nonwoven Feminine Hygiene Material

Figure 5:
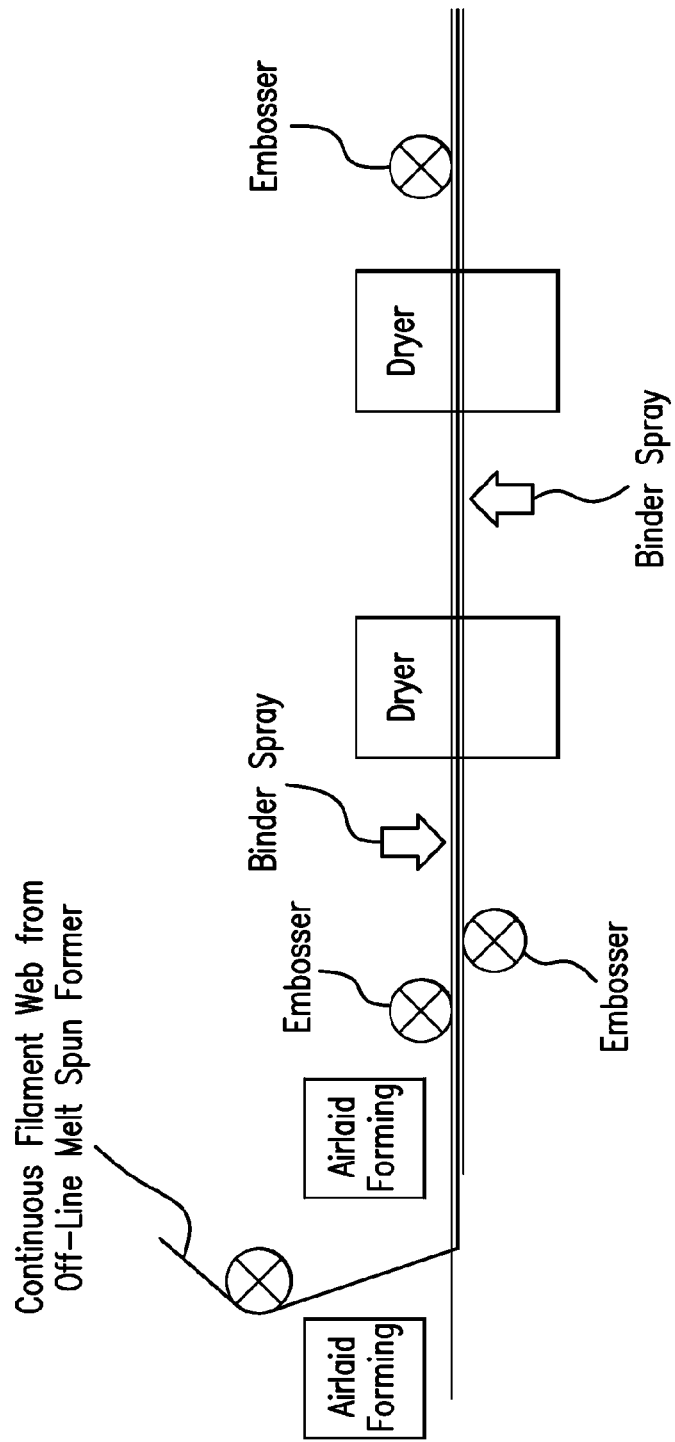
FIG. 5 illustrates a process schematic for an exemplary embodiment of a method for manufacturing a multilayer structure in accordance with the disclosed subject matter.

A two-layer nonwoven structure of Sample 3, similar to that shown in FIG. 2A, was formed using a pilot-scale drum-forming airlaid nonwoven machine, according to the process shown in FIG. 5.

The bottom layer of the Sample 3 structure includes softwood kraft cellulose fluff (Foley Fluffs-TAS, Georgia-Pacific) and the top layer of the Sample 3 structure was made of a web of continuous polypropylene filaments formed on a pilot-scale Reicofil meltblown nonwoven machine. The basic structural characteristics of the continuous filament web used for the top layer of the Sample 3 structure are given in Table 3. The basis weight of the cellulose fluff in the bottom layer was 36 gsm and the basis weight of the continuous filament web in the top layer had a basis weight of 20 gsm. The bottom and the top layers were bonded with a polymeric binder in the form of emulsion (Vinnapas 192, Wacker). The top and bottom layers each included 2.5% Vinnapas 192 binder based on dry weight of the total Sample 3 structure.

TABLE 3

| Characteristics | Value |
| --- | --- |
| Polymer Grade | Braskem CP 360 H Homopolypropylene |
| Basis Weight (gsm) | 20 |
| Filament average diameter (μm) | 3-14 |

Table 4 shows basic physical characteristics of the Sample 3 structure and of a commercial latex-bonded airlaid acquisition layer (Vicell 6609, Georgia-Pacific). The commercial acquisition layer can be used as an acquisition layer in a commercial feminine hygiene sanitary napkin (for example, Casino Ultra Normal). The thickness values shown in Table 4 were obtained using a Thwing Albert ProGage Thickness Tester at a pressure of 0.5 kPa and with a dwell time of 9.9 seconds.

TABLE 4

| Characteristics | Sample 3 | Commercial Acquisition Layer (Vicell 6609) |
| --- | --- | --- |
| Basis Weight (gsm) | 59 | 60 |
| Thickness (mm) | 0.79 | 0.76 |

Figure 6:
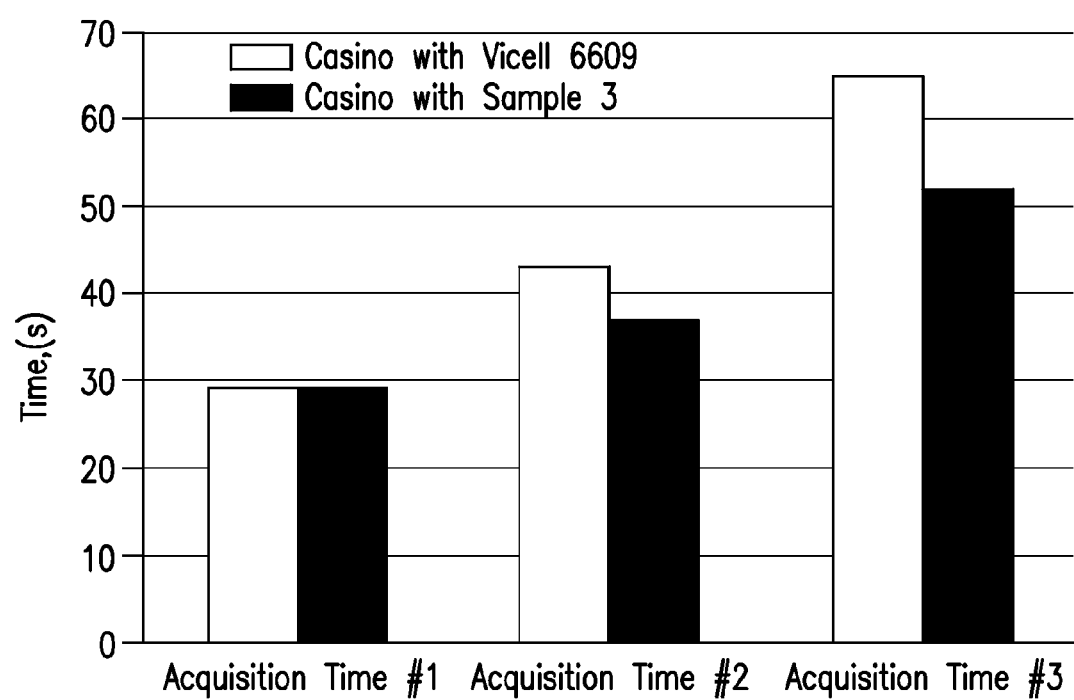
FIG. 6 is a graph comparing the liquid acquisition time for an exemplary embodiment of a multilayer structure in accordance with the disclosed subject matter against the liquid acquisition time of a conventional acquisition layer.

The Sample 3 structure and the commercial acquisition layer Vicell 6609 (Georgia-Pacific) were compared for their liquid acquisition characteristics. The acquisition tests were performed as described in Example 2. FIG. 6 illustrates improved acquisition performance of the Sample 3 structure with increased improvement at the second and third insult.

Figure 7:
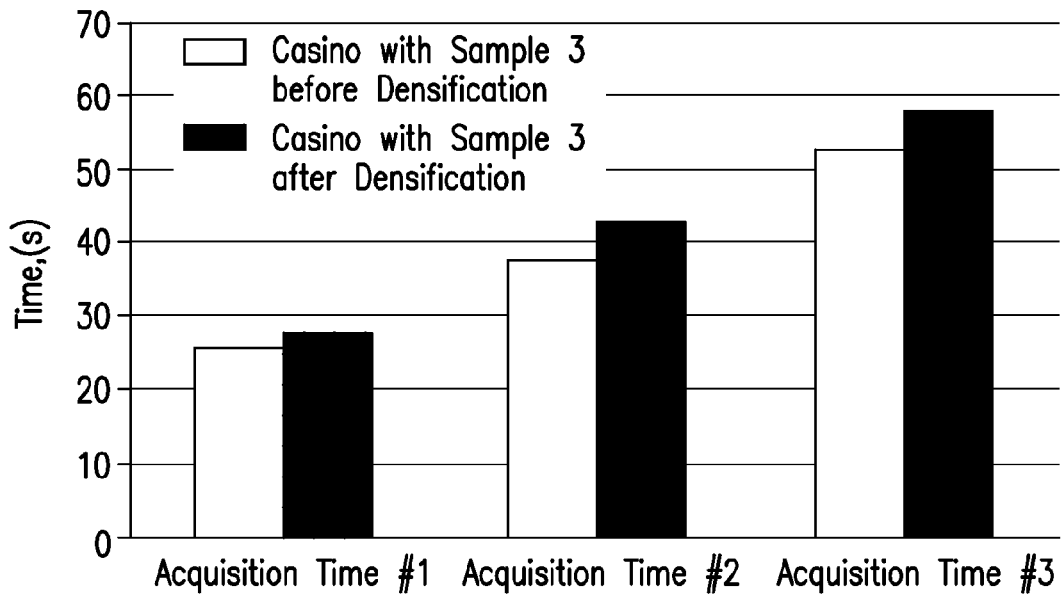
FIG. 7 is a graph comparing the liquid acquisition times for an exemplary embodiment of a multilayer structure in accordance with the disclosed subject matter before and after densification.
Figure 8:
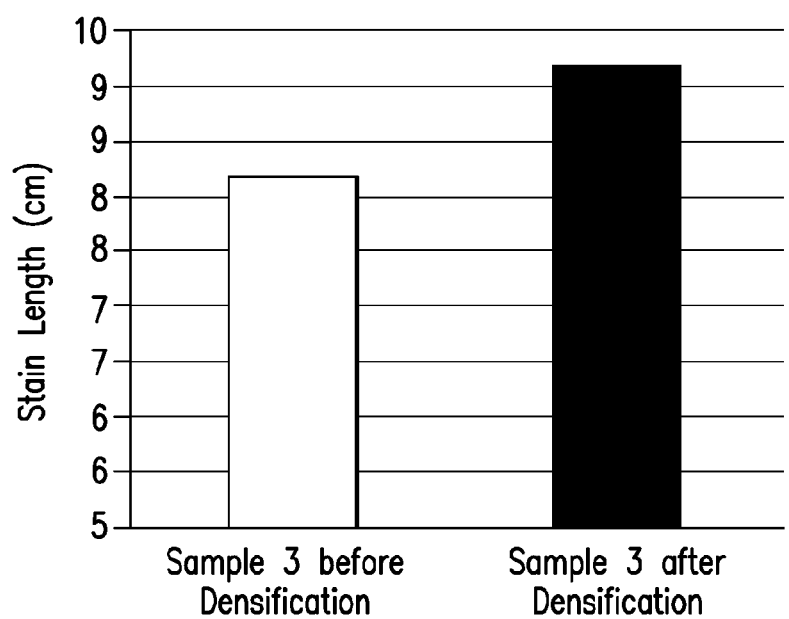
FIG. 8 is a graph comparing the stain lengths for an exemplary embodiment of a multilayer structure in accordance with the disclosed subject matter before and after densification.

Sample 3 was densified to a thickness of 0.34 mm (43% of the original thickness) and tested again for liquid acquisition performance following the procedure described in Example 2. The results are shown in FIG. 7. Surprisingly, substantial densification of Sample 3 had a relatively small effect on the obtained acquisition times. More densified, thinner absorbent layers are often desirable because they allow for designing thinner personal hygiene absorbent products. Without being bound by any particular theory, the continuous filament web top layer may be more resilient than the bottom layer composed mainly of cellulose fluff. Therefore, after densification of the Sample 3 structure the bottom layer became more densified than the top layer. As a result the top layer retained its good liquid acquisition capability. After densification, the more densified bottom layer improved liquid distribution which was demonstrated by longer wicking distance or length of the stain in the bottom layer after the liquid acquisition test. This effect is illustrated in FIG. 8.

Example 4: Nonwoven Feminine Hygiene Material

A two-layer nonwoven structure of Sample 4, similar to that as shown in FIG. 2A, was formed using a pilot-scale drum-forming airlaid nonwoven machine. This process is illustrated in FIG. 5.

The bottom layer of the Sample 4 structure includes softwood kraft cellulose fluff (Foley Fluffs-TAS, Georgia-Pacific) and the top layer of the Sample 4 structure was made of a web of continuous polypropylene filaments formed on Biax-Fiberfilm meltblown nonwoven machine. The basic structural characteristics of the continuous filament web used for the top layer of the Sample 4 structure are given in Table 5. The basis weight of the cellulose fluff in the bottom layer was 41 gsm and the basis weight of the continuous filament web in the top layer had a basis weight of 12 gsm. The bottom and the top layers were bonded with a polymeric binder in the form of emulsion (Vinnapas 192, Wacker). The top and bottom layers each included 5.8% Vinnapas 192 binder based on dry weight of the whole Sample 4 structure.

TABLE 5

| Characteristics | Value |
| --- | --- |
| Polymer Grade | ExxonMobil PP3155 Polypropylene |
| Basis Weight (gsm) | 12 |
| Filament average diameter (μm) | 3-72 |

Table 6 shows basic physical characteristics of the Sample 4 structure and of a commercial latex-bonded airlaid acquisition layer (Vicell 6609, Georgia-Pacific).

TABLE 6

| Characteristics | Sample 4 | Commercial Acquisition Layer (Vicell 6609) |
|---|---|---|
| Basis Weight (gsm) | 59 | 60 |
| Thickness (mm) | 0.76 | 0.76 |

Figure 9:
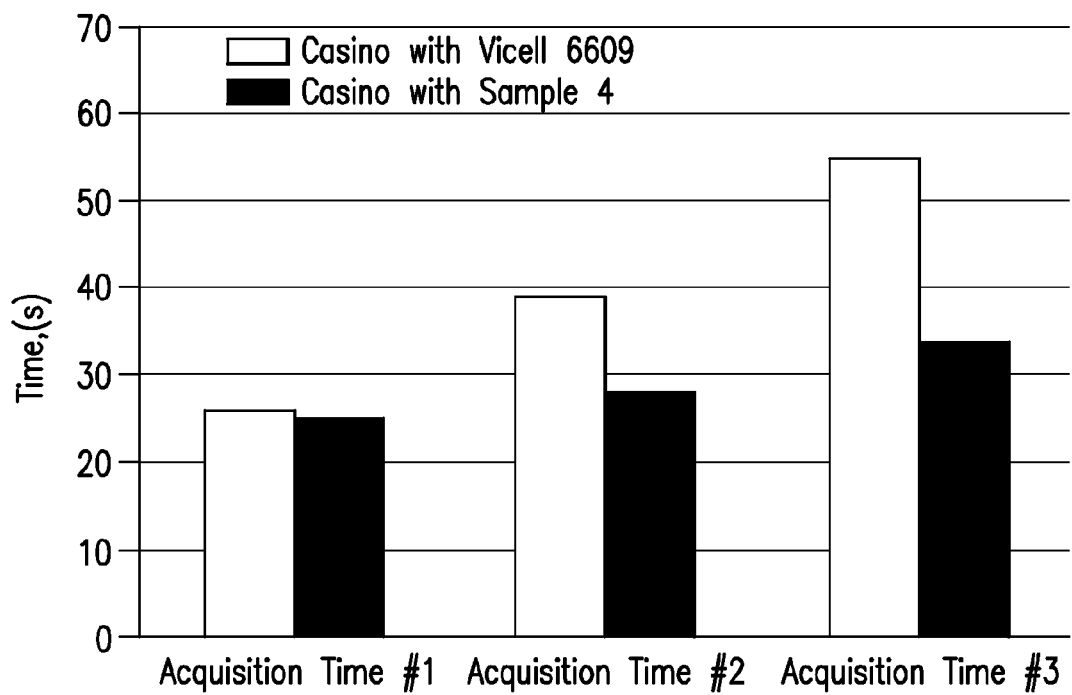
FIG. 9 is a graph comparing the liquid acquisition time for an exemplary embodiment of a multilayer structure in accordance with the disclosed subject matter against the liquid acquisition time of a conventional acquisition layer.

The Sample 4 structure and the commercial acquisition layer were compared for their liquid acquisition characteristics. The acquisition tests were performed as described in Example 2. FIG. 9 illustrates improved acquisition performance of the Sample 4 structure with increased improvement mainly at the second and third insult.

Example 5: Stress-Strain Characteristics of Traditional Airlaid Nonwovens

Figure 10:
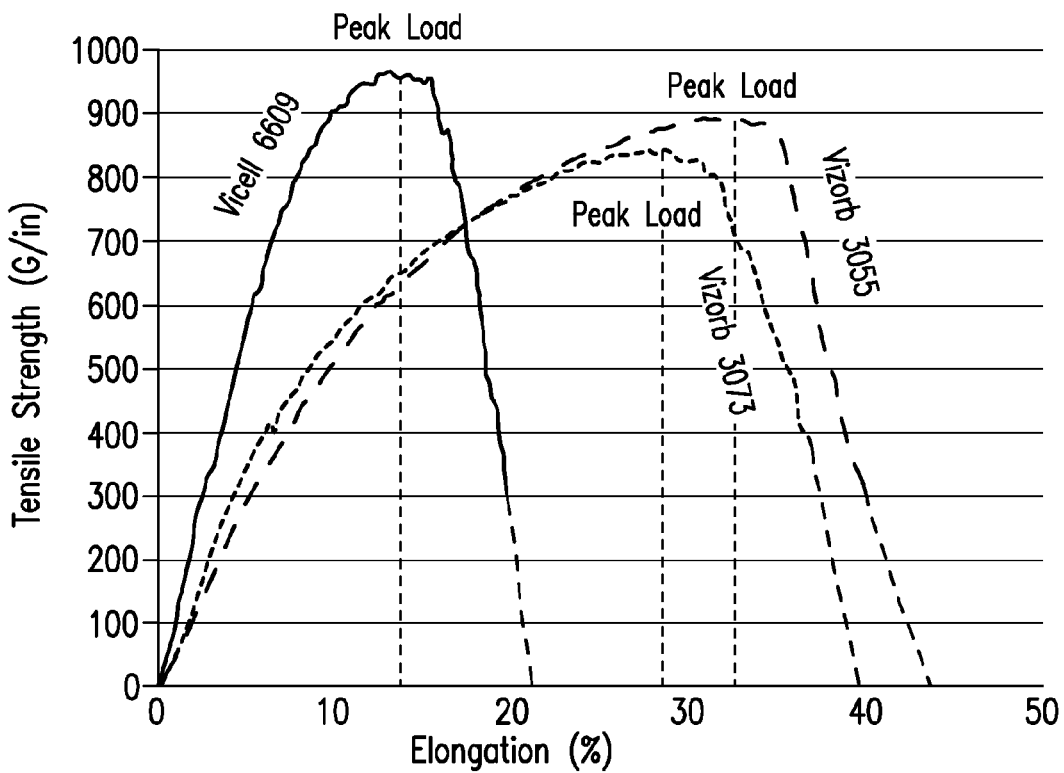
FIG. 10 is a graph showing stress-strain curves for conventional airlaid nonwovens.

The stress-strain curves of various airlaid nonwoven samples (Georgia-Pacific) are shown in FIG. 10. The stress-strain curves were generated using the Thwing Albert EJA Vantage Materials Tester and the MAP4 software. In all the Figures showing the stress-strain curves in this and other Examples the total elongation is measured by extrapolation of the obtained curves to "zero" load (intersection of the curves with the x-axis). Basic target characteristics of the tested samples are summarized in Table 7.

TABLE 7

| Product Name | Type of Airlaid | Basis Weight (gsm) | Thickness (mm) |
|---|---|---|---|
| Vicll 6609 | Latex-Bonded Airlaid | 61 | 0.77 |
| Vizorb 3055 | Multi-bonded Airlaid | 92 | 1.46 |
| Vizorb 3073 | Multi-bonded Airlaid | 62 | 0.97 |

The graphs in FIG. 10 show that the multi-bonded airlaid nonwovens which contain bicomponent binder fibers have higher elongation than the latex-bonded airlaid nonwoven which does not contain bicomponent binder fibers. Both types of airlaid samples, i.e. the multi-bonded and the latex-bonded airlaids have a similar shape of the stress-strain curves, that is, after reaching the elongation at the highest load the webs become quickly rather weak and eventually break. As a result, the elongation at the peak load of these nonwovens is higher than one half of their total elongation.

Figure 11:
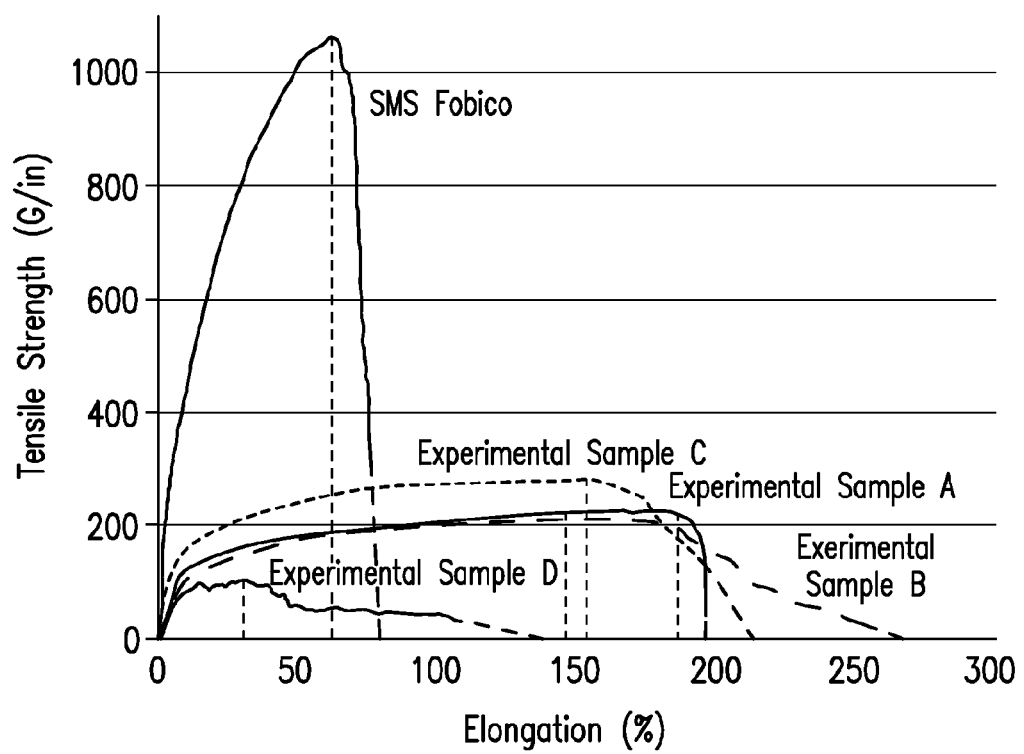
FIG. 11 is a graph showing stress-strain curves for nonwovens webs of continuous filaments.

Example 6: Stress-Strain Characteristics of Various Known Types of Nonwoven Webs The graphs in FIG. 11 show the stress-strain curves of some typical known nonwoven webs composed of continuous filaments. The basic information about these webs is summarized in Table 8.

TABLE 8

| Name | Producer | Equipment | Polymer | Type of Nonwoven | Basis Weight (gsm) | Filament Diameter (μm) |
|---|---|---|---|---|---|---|
| SMS Fobico (Commercial Product) | Fiberweb | — | Polypropylene | Spunbond-Meltblown-Spunbond | 17 | — |
| Experimental Sample A | Biax-Fiberfilm | Pilot-scale Biax-Fiberfilm | ExxonMobil PP3155 Polypropylene | Meltblown | 12 | 3-72 |
| Experimental Sample B | North Carolina State University | Pilot-scale Reicofil ® | Braskem CP 360 H Polypropylene | Meltblown | 15 | 3-14 |
| Experimental Sample C | North Carolina State University | Pilot-scale Reicofil ® | Braskem CP 360 H Polypropylene | Meltblown | 20 | 3-14 |
| Experimental Sample D | North Carolina State University | Pilot-scale Nordson/Hills | Braskem CP 360 H Polypropylene | Spunbond | 10 | 15-19 |

The stress-strain curves shown in FIG. 11 represent curves for an SMS (spunbond-meltblown-spunbond) web, meltblown nonwovens, and a spunbond nonwoven. The commercial SMS nonwoven is shown as SMS Fobico. Experimental Samples A, B, and C nonwovens represent three separate meltblown nonwovens. Experimental Sample D nonwoven represents a spunbond nonwoven. As shown by the stress-strain curves for Fobico and Experimental Samples A, B, and C, the elongation values at the peak loads are in each case more than half of their total elongation values. Interestingly, the stress-strain curve of Experimental Sample D shows the peak load is less than half the total elongation value. It is generally known that spunbond nonwovens are stronger than meltblown nonwovens and that their stretch is low. Therefore, one skilled in the art would expect that the stress-strain curve would be similar to that of the meltblown nonwovens, i.e., that the elongation at peak load would be greater than half of the total elongation. In this instance, Experimental Sample D was made using a modified spunbond process. It is worth noting that Sample D had a different pattern from that of the known spunbond nonwovens. Thus, it is thought that the process adjustments may have contributed to the shift of the stress-strain curve.

Figure 12:
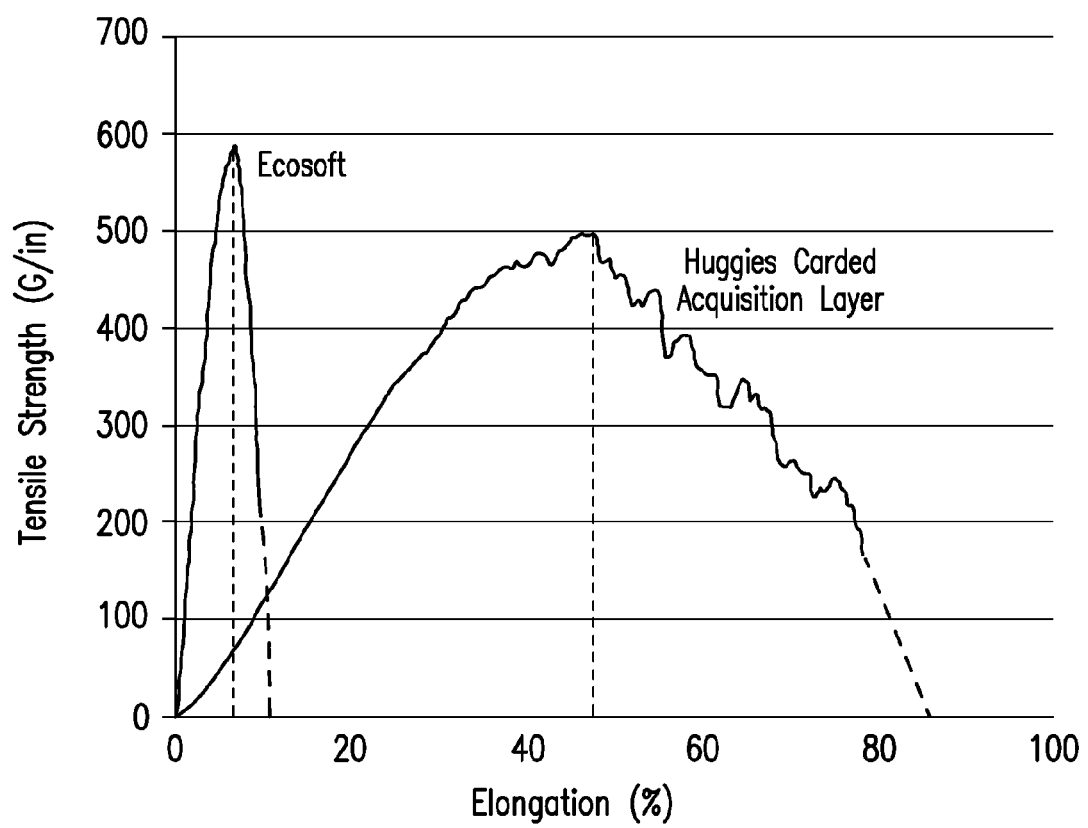
FIG. 12 is a graph showing stress-strain curves for a conventional wetlaid cellulose web and a conventional carded web.

One graph in FIG. 12 shows a stress-strain characteristics of the Ecosoft two-ply towel (Wausau Paper) which is a typical wet-laid cellulose web. The other graph is a stress-strain curve of a carded web used as an acquisition layer used in the Huggies diaper products (Kimberly-Clark). As seen in FIG. 12, the Ecosoft product has relatively low stretch. Both curves show the elongations at the peak load being more than a half of the total elongation.

Example 7: Stress-Strain Characteristics of Exemplary Nonwoven Structures

The raw materials used in this Example are listed in Table 9.

TABLE 9

| Raw Material | Type of Raw material | Maker of Raw Material |
|---|---|---|
| Experimental Sample B as listed in Table 8 | Continuous filament meltblown | North Carolina State University |
| GP 4825 | Cellulose fluff | Georgia-Pacific |
| Vinnapas 192 (used in Sample 5) | Binder emulsion | Wacker |
| Vinnapas LL1088 (used in Sample 6) | Binder emulsion | Wacker |
| Mowilith LDM 7717 (used in Sample 7) | Binder emulsion | Celanese |
| Dur-O-Set Elite Ultra (used in Sample 8) | Binder emulsion | Celanese |

Samples of nonwoven structures in accordance with the disclosed subject matter were made using a laboratory pad former, sprayed on both sides with binder emulsions and heat-cured in the laboratory through-air-dry oven. The curing temperature was 110° C. and time of curing was 5 min for either side of the sample after being sprayed with appropriate binder emulsion. Sample 5 was bonded with the Vinnapas 192 binder, Sample 6 was bonded with the Vinnapas LL1088 binder, Sample 7 was bonded with the Mowilith LDM 7717 binder and Sample 8 was bonded with the Dur-O-Set Elite Ultra binder. Each of the samples was a three-layer structure whose basic composition is described in Table 10. In each case the total target basis weight was 60 gsm and the target thickness was 0.80 mm.

TABLE 10

| Layer | Meltblown Web (gsm) | Cellulose Fluff (gsm) | Binder (dry gsm) |
|---|---|---|---|
| Top | N/A | 19.5 | 3.0 |
| Middle | 15 | N/A | N/A |
| Bottom | N/A | 19.5 | 3.0 |

Figure 13:
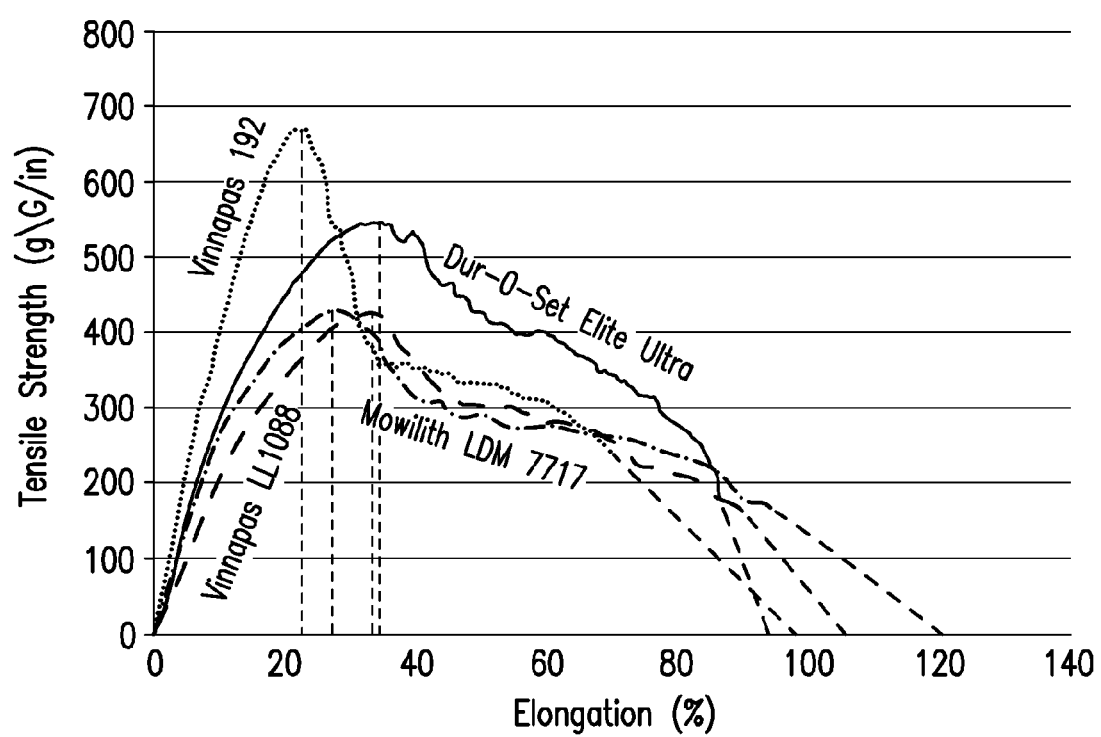
FIG. 13 is a graph showing stress-strain curves for exemplary embodiments of a three-layer nonwoven structure in accordance with the disclosed subject matter.

Thus prepared samples were tested for tensile strength and elongation. The samples were prepared for testing in such a way that the middle meltblown layer was pulled by the test instrument in the direction perpendicular to the machine direction of the pre-fabricated experimental meltblown web. FIG. 13 shows the stress-strain curves obtained for each of the dry samples. As seen in FIG. 13 all tested samples have the elongation at the peak load higher than 20% and total elongation higher than 80%. Their tensile strength at the peak load is higher than 400 G/in.

Figure 14:
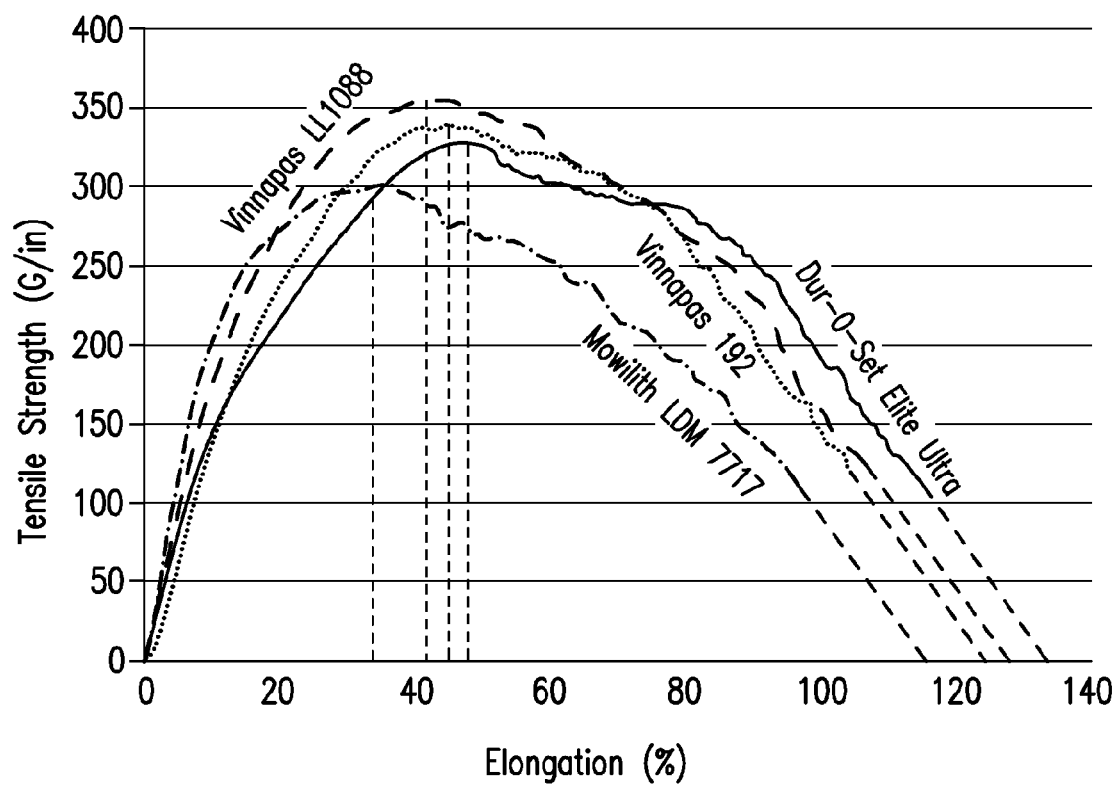
FIG. 14 is a graph showing stress-strain curves after wetting for exemplary embodiments of a three-layer nonwoven structure in accordance with the disclosed subject matter.

FIG. 14 shows the stress-strain curves of Samples 5, 6, 7 and 8 after wetting them in water for 20 seconds. As seen in FIG. 14 all tested samples have the elongation at the peak load higher than 30% and total elongation higher than 100%. Their tensile strength at the peak load is higher than 250 G/in.

Samples 5, 6, 7, and 8 exhibit the elongation at the peak load whose values are lower than half of their total elongation values. In contrast, known airlaid structures and other known nonwovens whose stress-strain curves are shown in other Examples do not exhibit such characteristics. This property can have practical significance when it is desirable to have a nonwoven material with high stretch for good in-use performance and at the same time to ensure that this material have sufficient tensile strength and sufficiently low elongation in the converting processes to make the finished product.

Example 8: Stress-Strain Characteristics of Exemplary Nonwoven Structures

Sample 9 is another example of a multilayer nonwoven structure in accordance with the disclosed subject matter. Sample 9 was made using laboratory pad-forming equipment and then cured in a lab air-through-dry oven twice at 110° C. for 5 minutes. The following raw materials were used for making Sample 9: (i) continuous filament meltblown web formed on a pilot-scale Reicofil machine with the Braskem CP 360H homopolypropylene (University of North Carolina); (ii) GP 4825 fluff (Georgia-Pacific); (iii) Trevira 1661 bicomponent fiber (6 mm, 2.2 den); and (iv) Vinnapas 192 binder emulsion (Wacker).

The total basis weight of Sample 9 was targeted at 60 gsm and its thickness was targeted at 0.80 mm. Table 11 summarizes the characteristics of the structure and composition of Sample 9.

TABLE 11

| Layer | Meltblown Web (gsm) | Cellulose Fluff (gsm) | Binder (dry gsm) | Bicomponent Fiber (gsm) |
|---|---|---|---|---|
| Top | N/A | 17.1 | 3 | 2.4 |
| Middle | 15 | N/A | N/A | N/A |
| Bottom | N/A | 17.1 | 3 | 2.4 |

Figure 15:
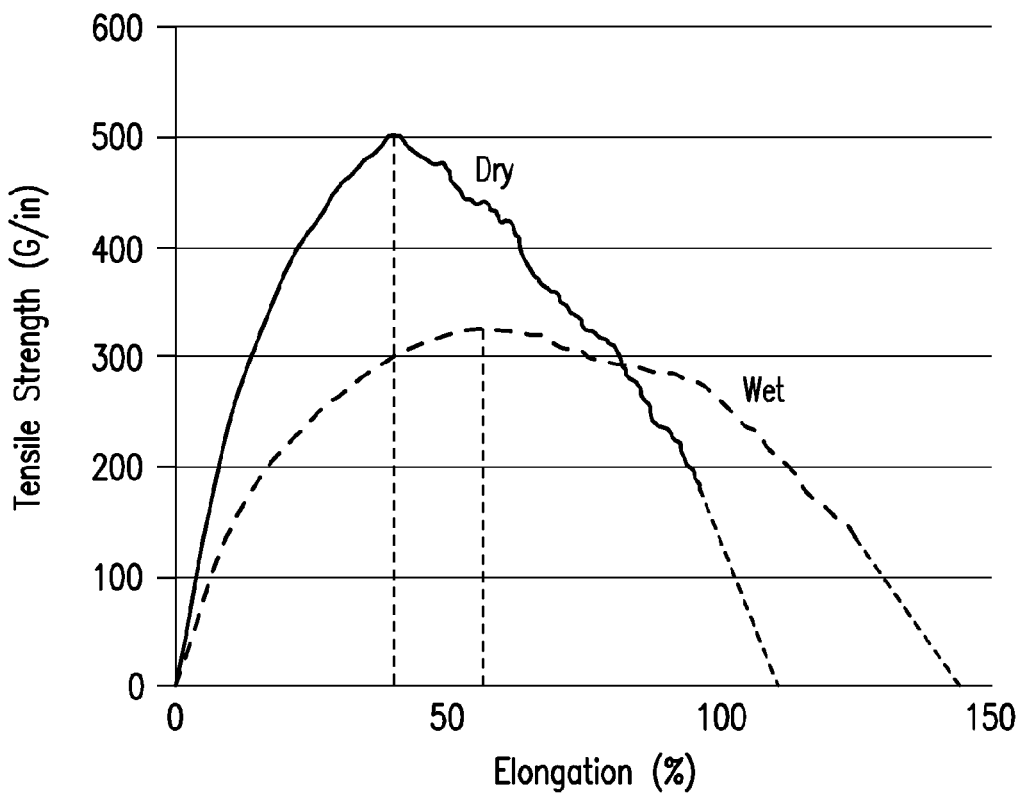
FIG. 15 is a graph showing stress-strain curves before and after wetting for an exemplary embodiment of a three-layer nonwoven structure in accordance with the disclosed subject matter.

Sample 9 was tested for its stress-strain characteristics both dry and after wetting it in water for 20 seconds just before being tested (FIG. 15). As seen in FIG. 15 the elongation of Sample 9 at the peak load is less than a half of its total elongation.

Example 9: Nonwoven Feminine Hygiene Material with Superabsorbent Powder

Samples of airlaid nonwoven structures with superabsorbent powder (Samples 10 and 11) were made using laboratory pad-forming equipment and then cured in a lab air-through-dry oven twice at 150° C. for 5 minutes.

The following raw materials were used for making Sample 10 and 11: (i) continuous filament meltblown web formed on a pilot-scale Reicofil machine with the Braskem CP 360H homopolypropylene (University of North Carolina); (ii) Foley Fluffs TAS fluff (Georgia-Pacific); (iii) Trevira 1661 bicomponent fiber (6 mm, 2.2 den); (iv) Vinnapas 192 binder emulsion (Wacker); and (v) BASF FEM33 superabsorbent powder.

Tables 12 and 13 summarize the characteristics of the structures and compositions, respectively, of Sample 10 of the present invention and of Sample 11 which is an example of a typical multi-bonded airlaid nonwoven web containing superabsorbent powder.

TABLE 12

| Layer | Meltblown Web (gsm)/ Filament Diameter (μm) | Cellulose Fluff (gsm) | Binder (dry gsm) | Superabsorbent powder (gsm) |
|---|---|---|---|---|
| Layer 1 (Top) | 20/3-14 | N/A | 5 | N/A |
| Layer 2 | N/A | 20 | N/A | N/A |

TABLE 12-continued

| Layer | Meltblown Web (gsm)/ Filament Diameter (μm) | Cellulose Fluff (gsm) | Binder (dry gsm) | Superabsorbent powder (gsm) |
|---|---|---|---|---|
| Layer 3 | N/A | N/A | N/A | 20 |
| Layer 4 (Bottom) | N/A | 50 | 5 | N/A |

TABLE 13

| Layer | Bicomponent Fiber (gsm) | Cellulose Fluff (gsm) | Binder (dry gsm) | Superabsorbent powder (gsm) |
|---|---|---|---|---|
| Layer 1 (Top) | 5.7 | 20 | 5 | N/A |
| Layer 2 | N/A | N/A | N/A | 20 |
| Layer 3 (Bottom) | 14.3 | 50 | 5 | N/A |

Figure 16:
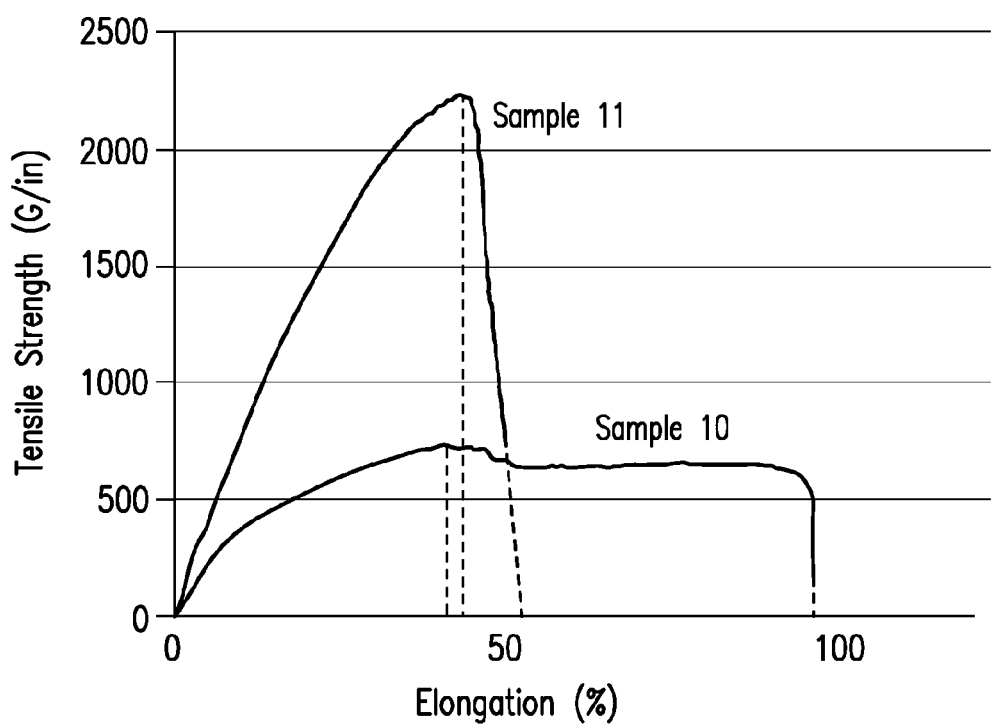
FIG. 16 is a graph comparing the stress-strain curve of an exemplary embodiment of a nonwoven web containing superabsorbent powder against the stress-strain curve of a conventional airlaid nonwoven web containing superabsorbent powder.

Samples 10 and 11 were characterized for their stress-strain characteristics (FIG. 16). As seen in FIG. 16, Sample 10 has lower tensile strength than Sample 11 but much higher elongation. The elongation at the peak load of Sample 10 is less than half of its total elongation. In contrast, the elongation at the peak load of Sample 11 is more than half of its total elongation.

Example 10: Stress-Strain Characteristics of Exemplary Nonwoven Structures

A three-layer nonwoven structure (Sample 4a) as shown in FIG. 2C was formed using a pilot-scale drum-forming airlaid nonwoven machine according to the process shown in FIG. 5. The top and bottom layers of the Sample 4a structure include softwood kraft cellulose fluff (Foley Fluffs-TAS, Georgia-Pacific) and the middle layer of the Sample 4a structure was made of a web of continuous polypropylene filaments formed on Biax-Fiberfilm meltblown nonwoven machine. The basic structural characteristics of the continuous filament web used for the middle layer of the Sample 4a structure are given in Table 4. The basis weight of the cellulose fluff in the bottom layer was 21 gsm and the basis weight of the continuous filament web in the middle layer had a basis weight of 12 gsm. The layers were bonded with a polymeric binder in the form of emulsion (Vinnapas 192, Wacker). The top and bottom layers each included 5.8% Vinnapas 192 binder based on dry weight of the total Sample 4a structure. The total basis weight of Sample 4a was 59 gsm and the thickness of Sample 4a was 0.76 mm.

Figure 17:
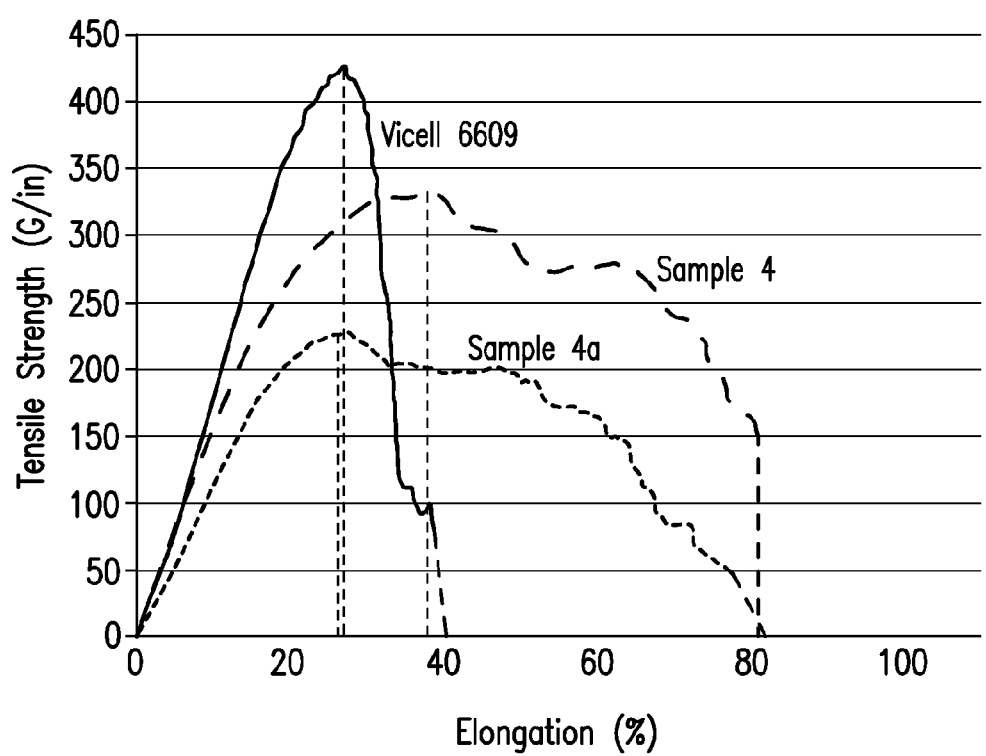
FIG. 17 is a graph comparing the stress-strain curves of exemplary embodiments of a two-layer nonwoven structure in accordance with the disclosed subject matter against the stress-strain curve of a conventional, commercially available airlaid structure.

Sample 4 described in Example 4, Sample 4a and a sample of Vicell 6609 were wetted in water for 10 seconds and then immediately tested for their stress-strain characteristics. The results are shown in FIG. 17. Sample 4 and Sample 4a exhibit the elongation at the peak load of which the values are lower than a half of their total elongation values. In contrast, Vicell 6609, which is a commercial latex-bonded airlaid product, does not exhibit the same behavior.

Example 11: Stress-Strain Characteristics Exemplary Nonwoven Structures

Three-layer nonwoven structures (Samples 12, 13 and 14) as shown in FIG. 2C were formed using a pilot-scale drum-forming airlaid nonwoven machine according to the process shown in FIG. 5. The basic characteristics of the continuous filament web layers located in the middle of these Samples are summarized in Table 14. The outer layers (top and bottom layers) of Samples 12, 13 and 14 were composed of Foley Fluffs TAS fluff (Georgia-Pacific) used in a target amount of 21.1 gsm for each of those layers. The top and bottom layers of Samples 12, 13 and 14 were sprayed with the Vinnapas 192 binder emulsion (Wacker) in each case in a target amount of 2.9 gsm based on dry basis weight of the binder. The basis weight and the thickness values of Samples 12, 13 and 14 are summarized in Table 15.

TABLE 14

| Sample # | Type of Continuous Filament Layer | Equipment | Basis Weight (gsm) | Filament Diameter (μm) | Type of Polymer |
|---|---|---|---|---|---|
| 12 | Spunbond | Hills | 10 | 15-19 | Braskem 360 H PP |
| 13 | Spunbond | Hills | 10 | 15-19 | Braskem 360 H PP |
| 14 | Melt Blown | Reicofil | 15 | 3-14 | Braskem 360 H PP |

TABLE 15

| Sample # | Measured Basis Weight (gsm) | Measured Thickness (mm) |
|---|---|---|
| 12 | 58 | 0.89 |
| 13 | 59 | 0.70 |
| 14 | 65 | 0.84 |

Figure 18:
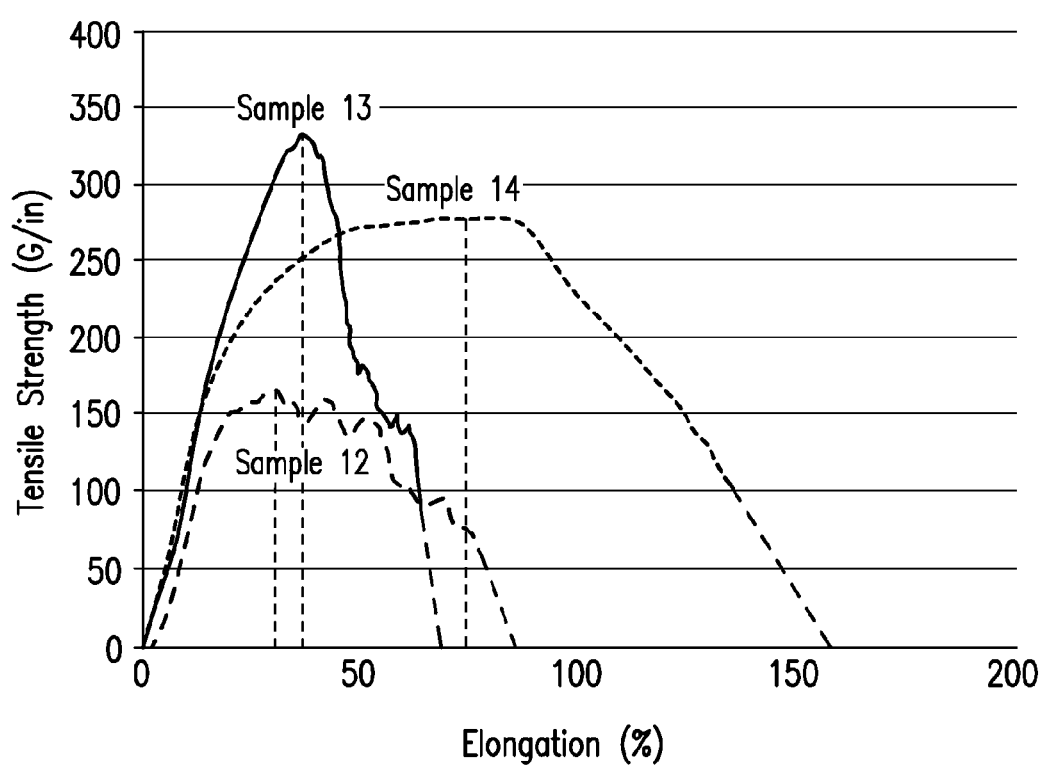
FIG. 18 is a graph showing the stress-strain curves of exemplary embodiments of a three-layer nonwoven structure in accordance with the disclosed subject matter.
Figure 19:
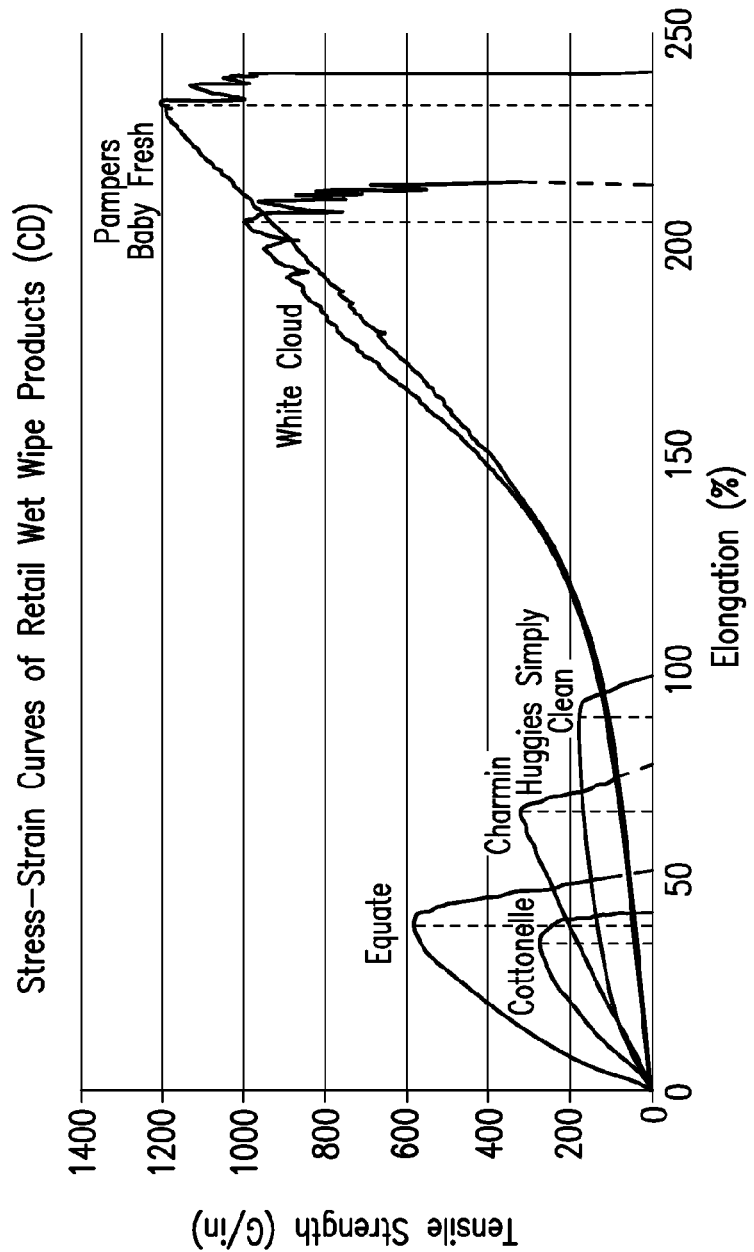
FIG. 19 is a graph showing the stress-strain curves of conventional, commercially available wet wipe products.
Figure 20:
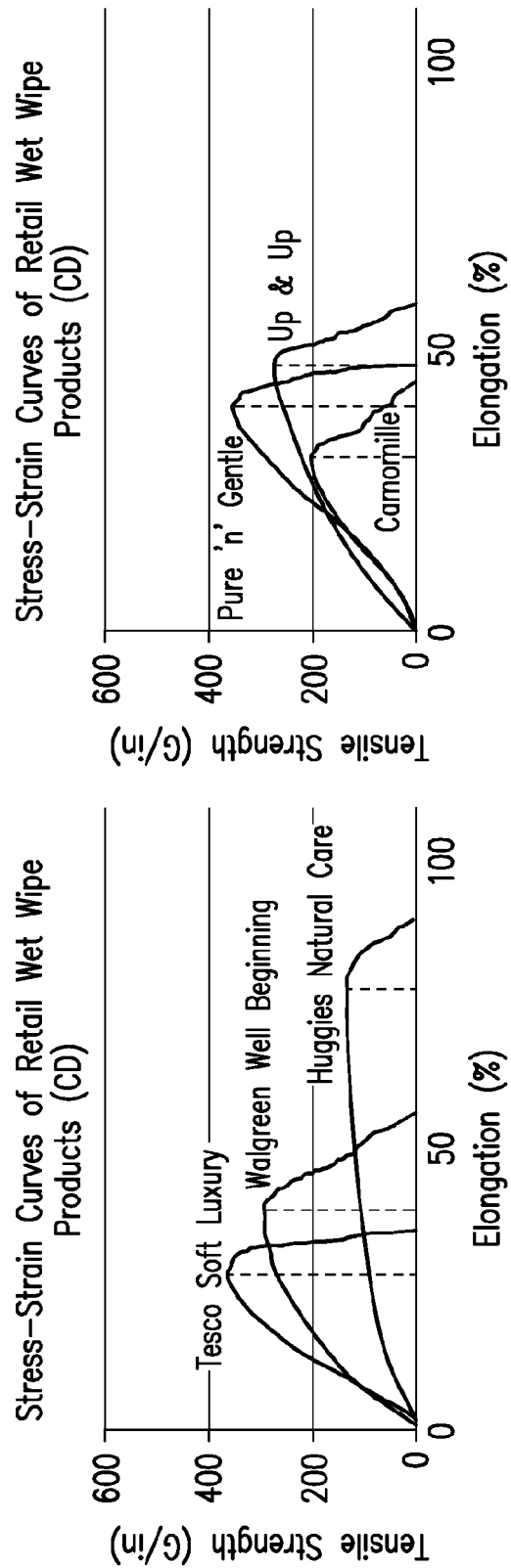
FIG. 20 is a graph showing the stress-strain curves of conventional, commercially available wet wipe products.
Figure 21:
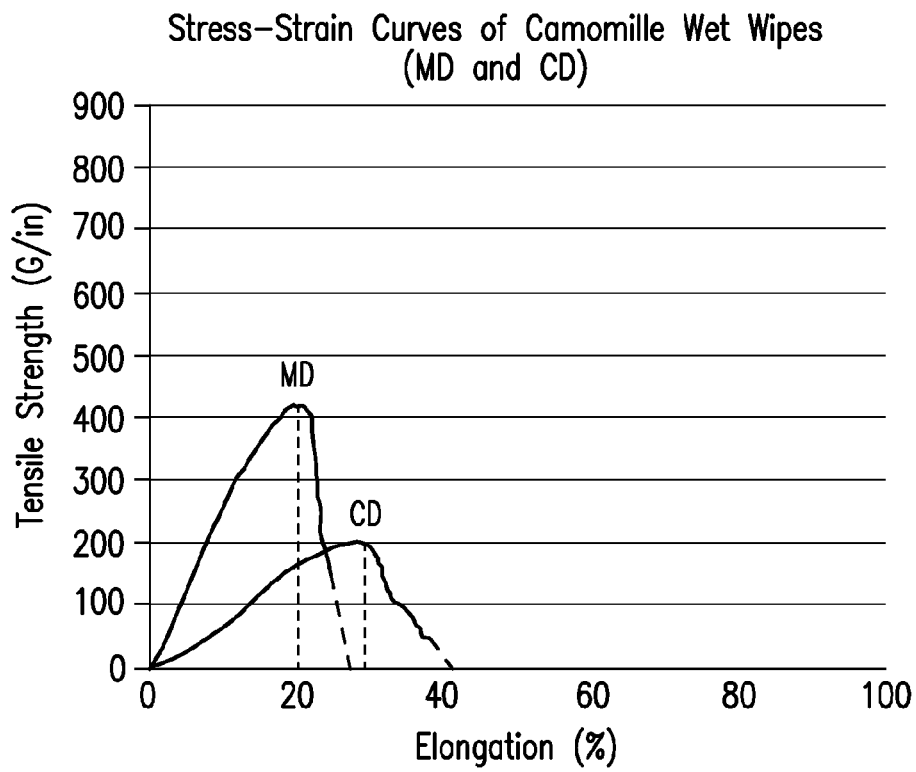
FIG. 21 is a graph showing the stress-strain curves of conventional, commercially available wet wipe products.
Figure 22:
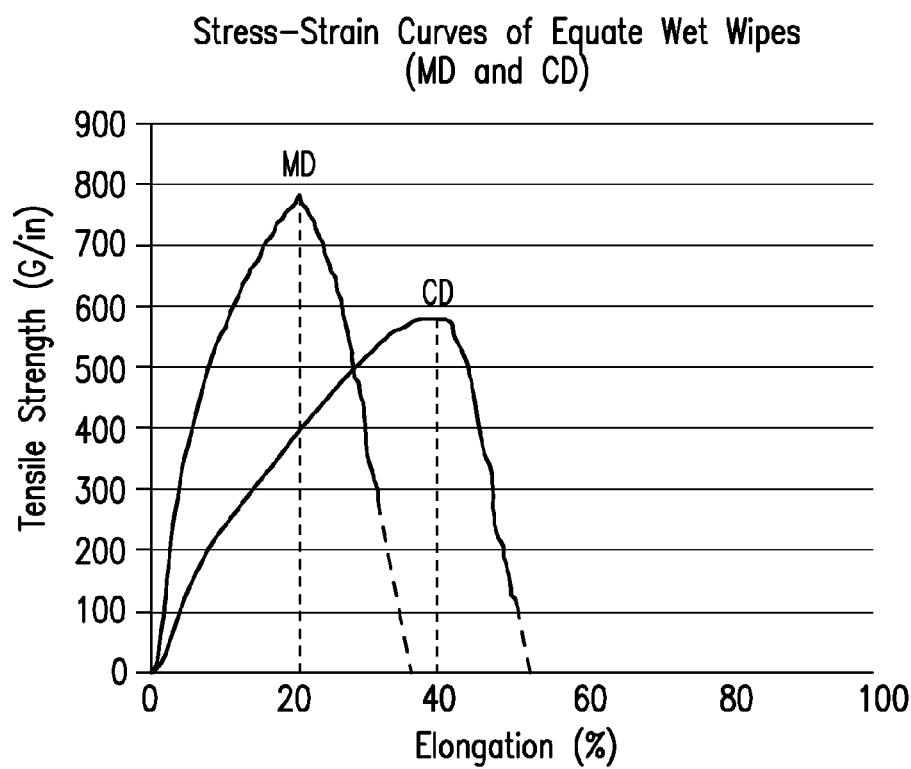
FIG. 22 is a graph comparing the stress-strain curve of a conventional, commercially available wet wipe product in the machine direction (MD) against the stress-strain curve of the conventional, commercially available wet wipe production in the cross-machine direction (CD).
Figure 23:
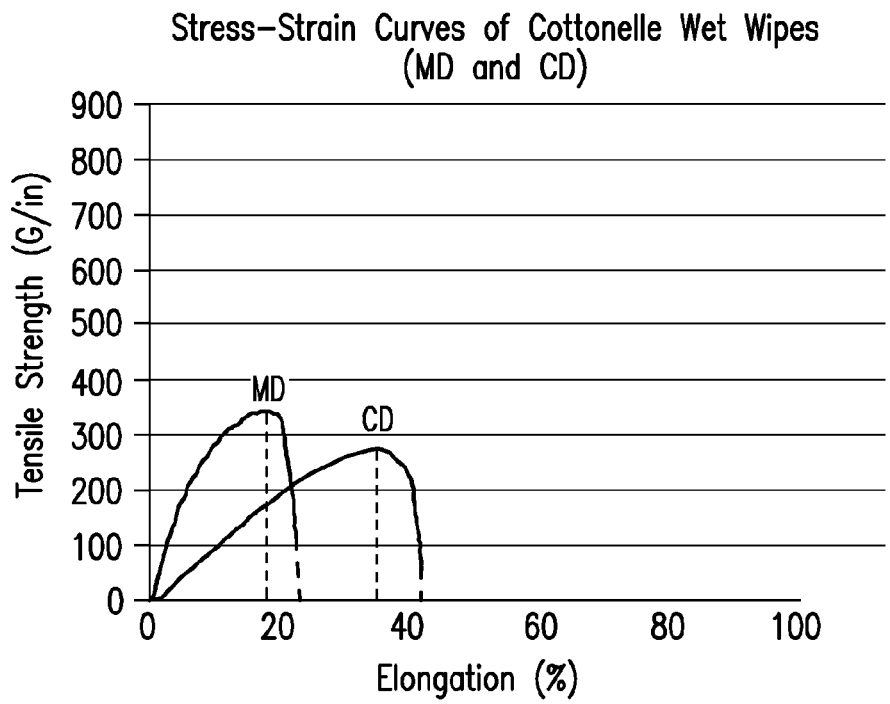
FIG. 23 is a graph comparing the stress-strain curve of a conventional, commercially available wet wipe product in the machine direction (MD) against the stress-strain curve of the conventional, commercially available wet wipe production in the cross-machine direction (CD).
Figure 24:
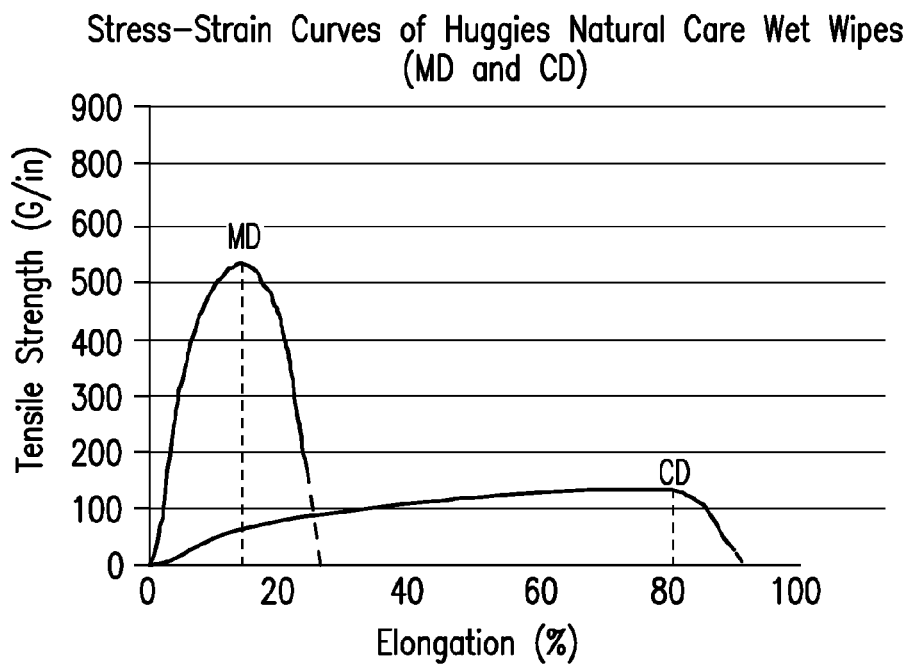
FIG. 24 is a graph comparing the stress-strain curve of a conventional, commercially available wet wipe product in the machine direction (MD) against the stress-strain curve of the conventional, commercially available wet wipe production in the cross-machine direction (CD).
Figure 25:
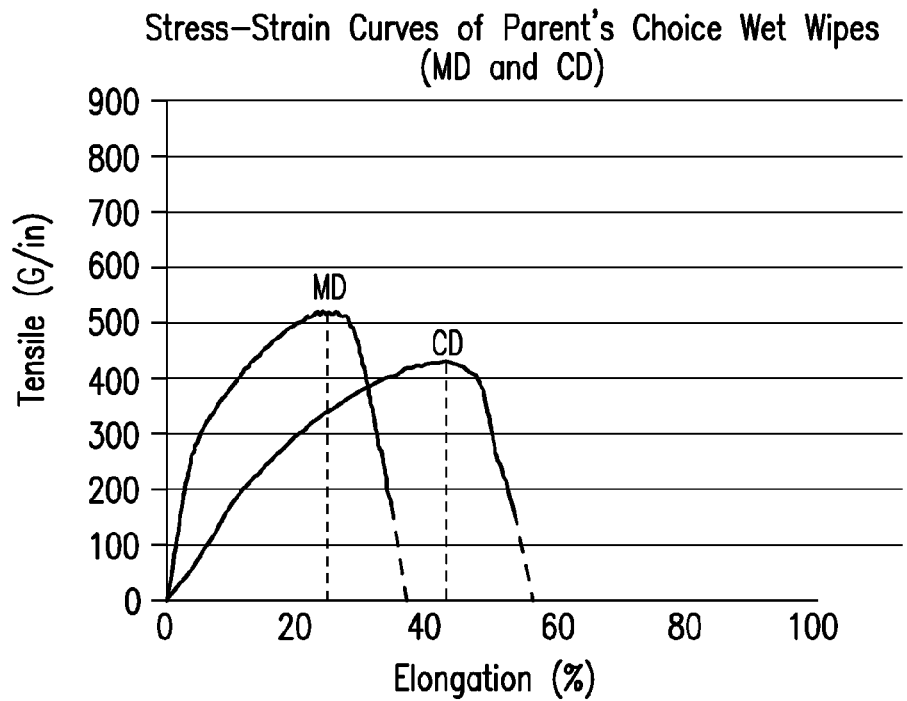
FIG. 25 is a graph comparing the stress-strain curve of a conventional, commercially available wet wipe product in the machine direction (MD) against the stress-strain curve of the conventional, commercially available wet wipe production in the cross-machine direction (CD).

Samples 12, 13 and 14 were tested for their stress-strain characteristics and the results are shown in FIG. 18.

Even though Sample 12 and Sample 13 have the same target composition and structure, the stress-strain curves are not identical due to different temperatures of curing. Sample 12 was cured at a lower temperature than Sample 13 which created less bonding of the Sample 12 structure. The temperature of curing can be used as one method for controlling the stress-strain characteristics of multilayer nonwoven structures in accordance with the disclosed subject matter.

Example 12: Stress-Strain Characteristics of Retail Wet Wipe Products

A range of retail wet wipe products made with various nonwoven materials including airlaid, spunlace and coform nonwovens were tested for their stress-strain characteristics. The wipes were tested in their cross-machine direction (CD) in which case generally the nonwovens products exhibit lower tensile strength and some of them were tested also in their machine direction (MD) in which case generally the nonwoven products exhibit higher tensile strength. The results of these tests are shown in FIGS. 19-25.

For each product tested as shown in FIGS. 19-25, the stress-strain curves show that the values of the elongation at the peak load are more than half of the respective total elongation values.

Similar behavior is seen for all the stress-strain curves for known nonwoven webs (FIGS. 10, 12, 19-25, the stress-strain curves for the commercial SMS and for the meltblown nonwoven Experimental Samples A, B and C in FIG. 11). In contrast, the multilayer nonwoven structures in accordance with the disclosed subject matter (FIGS. 13-15, Sample 10 in FIG. 16, Samples 4 and 4a in FIG. 17 and FIG. 18) exhibit elongation at peak load that is less than half of total elongation. As previously noted, FIG. 11 shows stress-strain curves of the Experimental Samples A, B, C and D of the continuous filament web structures which were used to prepare the multilayer nonwoven structures whose stress-strain characteristics are shown in FIGS. 13-15, in FIG. 16 (Sample 10) and in FIGS. 17 and 18 (Samples 4 and 4a). It is interesting to note that the Experimental Samples A, B and C exhibit the same general stress-stain pattern as other known nonwovens including the airlaid nonwovens even though their elongations and tensile strengths are usually quite different in absolute values.

Surprisingly, when the continuous filament web layers of the Experimental Samples A, B and C were combined with the airlaid nonwoven layers having stress-strain curves in which the values of the elongation at the peak load are more than half of the respective total elongation values, the resultant multilayer nonwoven structures acquired different characteristics. In particular, the multilayer structures have values of elongation at the peak load that are less than a half of the respective total elongation values. The practical significance of this is suggested in Example 7.

Figure 26:
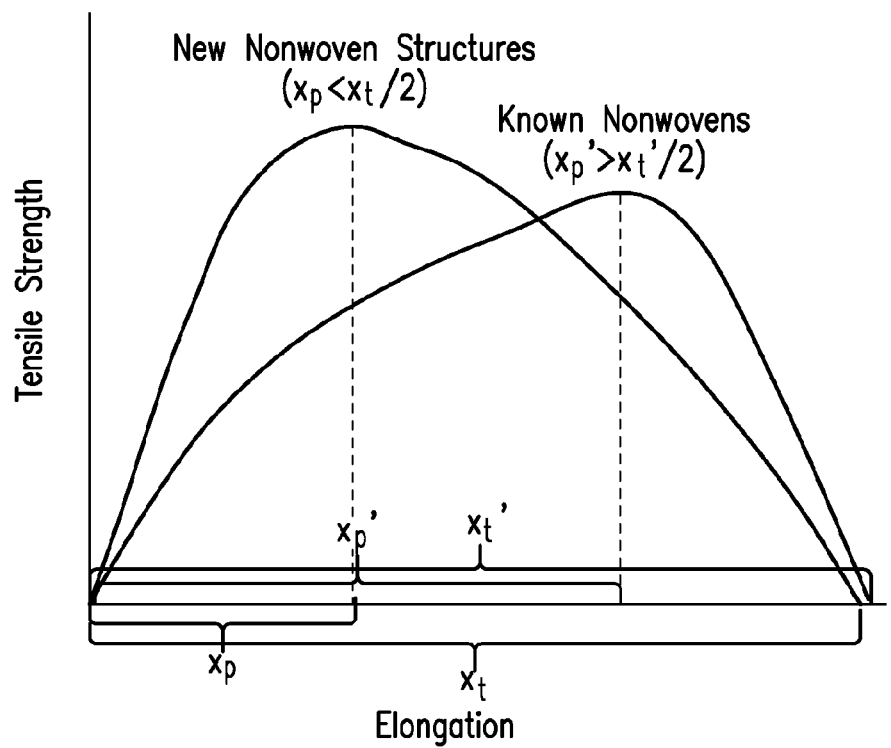
FIG. 26 is a graph showing the conceptual difference between stress-strain curves for multilayer structures in accordance with the disclosed subject matter and stress-strain curves for conventional, commercially available products for purposes of explanation.

Without being bound by any particular theory, one can hypothesize that the new stress-strain curve characteristics are due to the surprising synergistic effect of the components of the multilayered structure in which the relatively high stretch of the continuous filaments layer is combined with the relatively high strength of the layers comprising bonded short fibers. The graphs in FIG. 26 show these two different patterns of the stress-strain curves for the known nonwoven materials and for multilayer nonwoven structures in accordance with embodiments of the disclosed subject matter. This difference can be described mathematically in the following way. For the nonwoven structures in accordance with the disclosed subject matter:

$$x_p < x_t/2$$

where: $x_p$ is elongation at peak load and $x_t$ is total elongation. For known nowovens:

$$x_p' > x_t'/2$$

where: $x_p'$ is elongation at peak load and $x_t'$ is total elongation.

All patents, patent applications, publications, product descriptions and protocols, cited in this specification are hereby incorporated by reference in their entireties for all purposes. In case of a conflict in terminology, the present disclosure controls.

While it will become apparent that the disclosed subject matter herein described is well calculated to achieve the benefits and advantages set forth above, the presently disclosed subject matter is not to be limited in scope by the specific embodiments described herein. It will be appreciated that the disclosed subject matter is susceptible to modification, variation and change without departing from the spirit thereof. For instance, the nonwoven structure is generally described in the context of an airlaid process. However, non-airlaid processes are also contemplated.

What is claimed is:

1. A multilayer nonwoven material, comprising:
   a first layer comprising fibers and defining a first outer surface of the multilayer nonwoven material, wherein the fibers are coated with a binder on the first outer surface of the multilayer nonwoven material;
   a second layer comprising fibers and defining a second outer surface of the multilayer nonwoven material, wherein the fibers are coated with a binder on the second outer surface of the multilayer nonwoven material; and
   an intermediate layer between the first layer and the second layer comprising continuous filaments,
   wherein the multilayer nonwoven material has an elongation at peak load that is less than half a total elongation, and
   wherein the fibers in the first layer and second layer comprise cellulosic fibers.

2. The multilayer nonwoven material of claim 1, wherein the continuous filaments comprise bonded continuous filaments.

3. The multilayer nonwoven material of claim 2, wherein the continuous filaments are bonded by hydroentangling or thermal bonding.

4. The multilayer nonwoven material of claim 1, wherein the fibers are formed by an airlaid process.

5. The multilayer nonwoven material of claim 1, wherein the fibers are formed by a wet laid process.

6. The multilayer nonwoven material of claim 1, wherein the nonwoven material comprises an embossed pattern.

7. The multilayer nonwoven material of claim 1, wherein the nonwoven material comprises a surface treatment for improving wettability.

8. The multilayer nonwoven material of claim 1, further comprising a functional additive.

9. The multilayer nonwoven material of claim 8, wherein the functional additive is a superabsorbent particle.

10. The multilayer nonwoven material of claim 8, wherein the functional additive is selected from a group consisting of odor control agents, microbial agents, and fire retardant agents.

11. The multilayer nonwoven material of claim 1, wherein the continuous filaments comprise synthetic filaments.

12. The multilayer nonwoven material of claim 11, wherein the synthetic filaments comprise a material selected from a group consisting of polypropylene, polyethylene, and polyester.

13. The multilayer nonwoven material of claim 1, wherein the continuous filaments comprise bicomponent filaments.

14. The multilayer nonwoven material of claim 1, wherein the continuous filaments comprise natural polymer filaments.

15. The multilayer nonwoven material of claim 1, wherein the continuous filaments comprise regenerated cellulose filaments.

16. The multilayer nonwoven material of claim 1, wherein the continuous filaments comprise spunbond filaments.

17. The multilayer nonwoven material of claim 1, wherein the continuous filaments comprise meltblown filaments.

18. The multilayer nonwoven material of claim 1, wherein the cellulosic fibers comprise natural fibers.

19. The multilayer nonwoven material of claim 1, wherein the cellulosic fibers comprise wood pulp fibers.

20. The multilayer nonwoven material of claim 1, wherein the fibers comprise regenerated cellulose fibers.

21. The multilayer nonwoven material of claim 1, wherein the fibers of the first layer and the second layer further comprise synthetic fibers.

22. The multilayer nonwoven material of claim 1, wherein the fibers comprise short fibers.

23. The multilayer nonwoven material of claim 1, further comprising one or more additional layers comprising bonded continuous filaments.

24. The multilayer nonwoven material of claim 1, further comprising one or more additional layer comprising bonded fibers.

25. A wipe comprising the multilayer nonwoven material of claim 1.

26. The wipe of claim 25, wherein the wipe is one of a dry wipe, a wet wipe, a personal care wipe, or an industrial wipe.

27. A personal care product comprising the nonwoven material of claim 1.

28. The personal care product of claim 27, wherein the personal care product is one of a diaper, a feminine care product, or an adult incontinence product.

29. A method for forming a multilayer nonwoven material comprising:
producing a first layer comprising fibers and defining a first outer surface of the multilayer nonwoven material, wherein the fibers are coated with a binder on the first outer surface of the multilayer nonwoven material;
producing a second layer comprising fibers and defining a second outer surface of the multilayer nonwoven material, wherein the fibers are coated with a binder on the second outer surface of the multilayer nonwoven material;
producing an intermediate layer between the first layer and the second layer comprising continuous filaments; and
binding the intermediate layer to each of the first layer and the second layer,
wherein the multilayer nonwoven material has an elongation at peak load that is less than half a total elongation, and
wherein the fibers in the first layer and second layer comprise cellulosic fibers.

30. The method of claim 29, wherein producing the intermediate layer comprises binding the continuous filaments by hydroentangling or thermal bonding.

31. The method of claim 29, wherein producing the intermediate layer comprises spunbonding.

32. The method of claim 29, wherein producing the intermediate layer comprises meltblowing.

33. The method of claim 29, wherein producing the first and/or second layer comprises using a airlaid process.

34. The method of claim 29, wherein producing the first and/or second layer comprises using a wet laid process.

35. The method of claim 29, further comprising adding a functional additive to the nonwoven material.

36. The method of claim 29, further comprising embossing the nonwoven material with a pattern.

37. The method of claim 29, further comprising treating the nonwoven material with a surface treatment to improve wettability.

* * * * *